United States Patent [19]

Madou et al.

[11] Patent Number: 4,795,968
[45] Date of Patent: Jan. 3, 1989

[54] GAS DETECTION METHOD AND APPARATUS USING CHEMISORPTION AND/OR PHYSISORPTION

[75] Inventors: Marc Madou, Palo Alto; Arden Sher, Foster; Christopher J. Spindt, Menlo Park, all of Calif.

[73] Assignee: SRI International, Menlo Park, Calif.

[21] Appl. No.: 880,555

[22] Filed: Jun. 30, 1986

[51] Int. Cl.⁴ .................... G01R 27/26; G01R 27/02
[52] U.S. Cl. ........................... 324/61 R; 324/65 R; 324/71.1; 338/34; 338/35; 204/1 T
[58] Field of Search .............. 324/65 R, 60 CD, 71.1, 324/92, 57 R, 64, 71.5, 60 R, 60 C, 61 R; 338/34, 14, 35, 13; 204/15, 1 Y, 421, 424, 430, 431, 1 T

[56] References Cited

U.S. PATENT DOCUMENTS

| | | | |
|---|---|---|---|
| 3,719,564 | 5/1971 | Lilly et al. | 204/1 X |
| 4,025,892 | 5/1977 | Pompei et al. | 338/35 |
| 4,039,941 | 8/1977 | Morrison | 324/71.1 |
| 4,190,990 | 2/1979 | Pompei kato de Warrens | 327/71.1 |
| 4,314,996 | 2/1982 | Sekido et al. | 338/34 |
| 4,482,581 | 11/1984 | Lorin et al. | 338/35 |
| 4,580,439 | 4/1986 | Manaka | 338/34 |
| 4,594,869 | 6/1986 | Fukushiria et al. | 338/34 |

OTHER PUBLICATIONS

Bard et al, "Electrochemical Methods", New York, 1980, pp. 316-369.

Primary Examiner—John F. Niebling
Assistant Examiner—Ben C. Hsing
Attorney, Agent, or Firm—Lowe, Price, Leblanc, Becker & Shur

[57] ABSTRACT

Gas species are detected with a capacitor having a solid, ionic dielectric excited by an AC voltage in the range from 0.01-30 Hz, with an amplitude of 1-100 millivolts to allow physisorption processes and/or with an AC voltage in the same frequency range and amplitudes from 0.01-3 volts to achieve chemisorption reactions. The AC impedancae of the capacitor is detected for both physisorption and chemisorption excitation to determine gas species and concentration. In chemisorption, diode like action occurs, and is detected by AC harmonic detection processes. The surface of the dielectric on which the gas is incident is overlaid with a grid or porous electrode, fabricated of inert metal or a catalyst which causes the capacitor to enable preferential adsorption by the dielectric of certain materials, to indicate the presence of certain gases. Plural capacitors, having different adsorption characteristics in response to different gases facilitates detection of plural gases. The dielectric is a rare earth fluoride, preferably lanthanum fluoride. The AC impedance of the capacitor provides the specie and concentration indications.

94 Claims, 6 Drawing Sheets

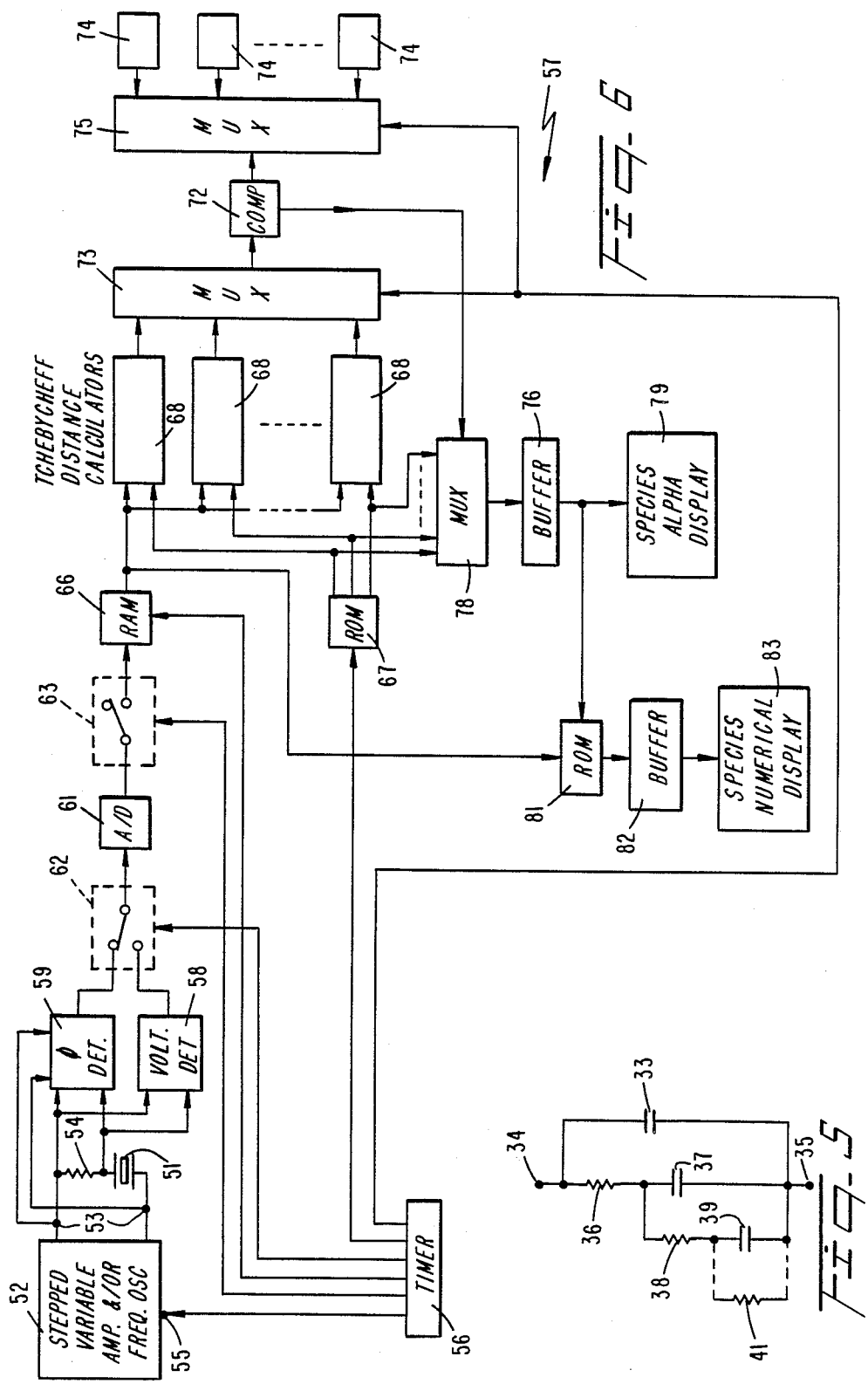

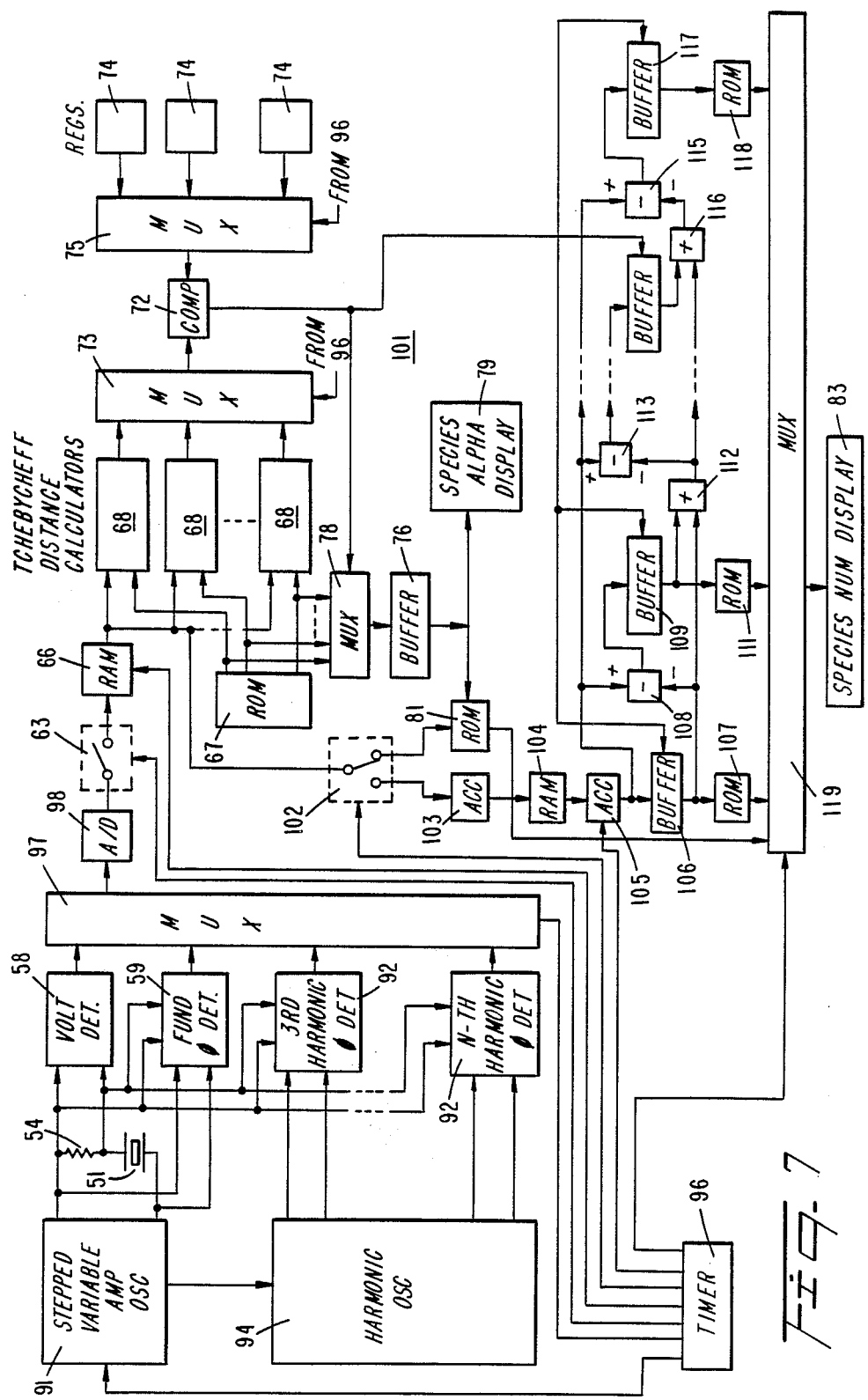

GAS DETECTION METHOD AND APPARATUS USING CHEMISORPTION AND/OR PHYSISORPTION

TECHNICAL FIELD

The present invention relates generally to gas detection methods and apparatus using capacitors having solid electrolyte dielectrics and more particularly to such a method and apparatus wherein a capacitor is energized by an AC source to measure chemisorption and/or physisorption effects.

BACKGROUND ART

One type of proposed prior art gas detector employs capacitors having a solid electrolyte, i.e., ionic, dielectrics, such as lanthanum fluoride ($LaF_3$). In the past, such gas detectors have been operated in the DC potentiometric method wherein a DC voltage applied between electrodes of the capacitor is modified as a function of the type and amount of gas incident on the dielectric. The DC potentiometric method, however, has the disadvantage of drift in the measuring apparatus and offset due to a polarizing effect of the DC voltage applied to the electrodes. These phenomena have a tendency to adversely affect the accuracy of quantitative and qualitative readings from the detector.

Certain types of the proposed prior art gas detectors employing solid electrolyte dielectrics have required the dielectric to operate at an elevated temperature. This disadvantage, which does not occur with lanthanum fluoride, decreases the efficiency of the detector because of the power required to supply the heat to elevate the dielectric temperature. The prior art gas detection apparatus and methods employing capacitors with solid electrolyte dielectrics have only generally been able to detect a very limited number of gases.

It is desirable to detect humidity of an ambient atmosphere through the use of capacitors having solid electrolyte dielectrics. However, prior art structures employing capacitors with solid electrolyte dielectrics for humidity detection have been plagued with inaccuracies because ambient environment temperature changes affect the capacitor impedance.

It is, accordingly, an object of the present invention to provide a new and improved method of and apparatus for detecting gases through the use of capacitors having solid electrolyte, i.e., ionic, dielectrics.

Another object of the present invention is to provide a new and improved gas detecting method and apparatus employing a capacitor having a solid electrolyte dielectric which is responsive to a relatively large number of gases, to provide accurate quantitative and qualitative information regarding said gases.

A further object of the present invention is to provide a new improved gas detecting method and apparatus employing a capacitor with a solid electrolyte dielectric capable of accurate quantitative and qualitative analyses at room temperature.

A further object of the invention is to provide a new and improved temperature and/or humidity detector that is accurate over a wide range of temperatures and which employs a capacitor having a solid electrolyte dielectric.

An additional object of the invention is to provide a new and improved method of and apparatus for accurately providing quantitative and qualitative information of ambient gases, wherein a capacitor employing a solid electrolyte dielectric is operated at room temperature.

DISCLOSURE OF INVENTION

In accordance with one aspect of the present invention, a new and improved gas detecting method and apparatus includes a capacitive means with a solid electrolyte, i.e., ionic, dielectric that is operated to have physisorption and/or chemisorption reactions with gases to be detected. Physical adsorption, referred to herein as physisorption, depends upon the physical or van der Waals forces of attraction between a solid adsorbent and the adsorbate molecules. Molecules with permanent dipole moments can interact with a solid dielectric in another type of physiosorption process that yields slightly stronger surface bonds but still leaves the molecules intact. There is little chemical specificity in physisorption so that any gas tends to be adsorbed on any solid if the solid is at a sufficiently low temperature or the gas is at a sufficiently high pressure. In chemisorption a chemical reaction occurs in a mixture of plural gases incident on an adsorber that may or may not be a dielectric. A product of the reaction is adsorbed by the adsorber. In certain embodiments the adsorber for the chemisorption reaction is a catalytic electrode on a dielectric. The gases are held by chemical forces on the adsorber. The chemical reactions may be modified by electric fields present at the gas/surface interface.

In physisorption processes of the present invention, molecules of the gas to be detected which are incident on a surface of the solid electrolyte dielectric modify the space charge at that surface. The dielectric surface exposed to the molecules adsorbs the molecules, resulting in surface effects inducing changes in the solid dielectric between a pair of electrodes of the capacitor. The space charge modification is indicated by effectively monitoring the impedance of the capacitor between the capacitor electrodes.

The physisorption effect or reaction is particularly adapted to detect gases having polar molecules, e.g., $H_2O$ and $H_2S$. The physisorption effect is monitored by connecting a relatively low ampltude voltage, preferably AC, across the capacitor electrodes. The voltage across the electrodes is kept small enough to prevent field assisted chemisorption, and is typically in the range from 1-100 mv. The physisorption process is independent of the nature of the applied voltage and can be measured as a transient current response to a pulsed DC voltage or in response to an applied AC voltage. It is preferable to use the AC detection mode so products of unwanted side reactions are alternately absorbed and repelled, i.e., desorbed, from the dielectric surface during each cycle of the AC source. Typically, 30 Hz is the maximum frequency for the space charge response to physisorption process; for practical applications, the frequency is in the range of about 0.03 to 30 Hz.

For certain gases the physisorption reaction is temperature dependent. This is particularly true for water vapor, the gas which is sensed to determine ambient relative humidity. The temperature of the sensor is measured by energizing the capacitor with an AC voltage having an amplitude in a range that causes the space charge to vary. The AC voltage is in a first relatively high frequency range to which a first equivalent circuit resistor and a first equivalent circuit capacitor of the gas detecting capacitor are respective. The first equivalent circuit resistor and capacitor are in a first series equivalent circuit and respectively represent the ionic resistance of the dielectric due to the motion of ionic holes across the dielectric thickness and the space charge layer of ionic holes in the dielectric. The first frequency range is higher than that which would cause the surface space charge to contribute to the measured signal. For example, the application of a voltage having an amplitude in the 1-100 mv range, at a frequency of 1 kHz across the electrodes of a capacitor having a solid electrolyte dielectric produces a response that is indicative of the ambient temperature to which the dielectric is subjected but which is insentive to ambient humidity. This response is combined with a response of the capacitor to an energization voltage having an amplitude in the 1-100 mv range and a frequency in the 0.03-30 Hz range to derive an indication of relative humidity that can be corrected to account for the temperature.

In the chemisorption process according to the present invention, molecules of the gas being detected chemically react under the influence of an AC voltage applied to the solid electrolyte dielectric surface or with a catalyst on the dielectric. The chemisorption reactions can be categorized into several classes, designated as A, B, C and D herein. The chemisorption reactions of classes A, B, C and D modify the values of a second equivalent circuit capacitor and a second equivalent circuit resistor connected in a second series equivalent circuit shunting the first equivalent circuit capacitor. Because the value of the second equivalent circuit capacitor is much greater than that of the first equivalent circuit capacitor the component values of the second equivalent circuit enable the gas parameters to be detected in response to impedance changes at the detector terminals resulting from the chemisorption reactions. The impedance changes are detected by applying to the detector an electric source in a second frequency range that is considerably lower than the first range. The component values of the first equivalent circuit are not effectively changed by the excitation at the second range. The four classes are categorized as follows:

Class A, the analyte gas reacts directly with the $LaF_3$ surface even for low AC or DC amplitude electric fields, so the effect is independent of the amplitude of any applied AC or DC voltages;

Class B, the analyte gas reacts independently of the amplitude of an applied AC or DC voltage, but only in the presence of a catalyst (usually the upper electrode material);

Class C, the analyte gas is driven by an electric field applied to the sensor dielectric which causes the sensor action to be voltage amplitude dependent (examples of such analyte gases are non-polar oxidizing gases $O_2$, $SO_2$, $NO_2$, etc.);

Class D, the analyte gas can only be detected in the presence of a second gas species incident on the dielectric (examples of such analyte gases are hydrocarbons, $CH_4$, etc.).

In the chemisorption process a capacitor containing a solid electrolyte dielectric is energized with an AC voltage in the second range and having a sufficiently large amplitude to cause the formation of a negative oxygen ion ($O^-$) species at the dielectric surface. The amplitude required to form the $O^-$ species differs for different gases. With a good catalyst the $O^-$ species can be made to react with hydrocarbons to provide a novel room-temperature hydrocarbon sensor. The voltage cannot be so great as to cause a breakdown across the solid dielectric. The frequency of the AC voltage inducing the chemisorption process must be sufficiently low to sweep the molecules into the dielectric and to repel the molecules during each cycle of the source. Hence, the frequency and amplitude of the AC chemisorption excitation are typically in the ranges of about 0.1 to 3 volts and about 0.03 to 30 Hz.

In the chemisorption process, oxygen is adsorbed on the dielectric surface. The adsorbed oxygen captures an electron of a metal, catalytic electrode on the dielectric, causing oxygen ions to be formed on the dielectric surface to increase the conductivity of the dielectric. When a reducing gas, such as methane ($CH_4$), is detected the reducing gas reacts with the ionized oxygen to decrease the dielectric conductivity.

Gas sensors employing capacitors with solid electrolyte, i.e., ionic, dielectrics utilizing the chemisorption process have been previously developed. Such chemisorption based gas detectors have been operated in the DC amperometric mode and have employed rare earth fluorides as the dielectric. Because the DC amperometric mode has been utilized, impurities have been permanently driven into the bulk dielectric to adversely affect the performance and accuracy of the sensor. In particular a back contact, i.e., a contact that abuts against a face of the dielectric that is not exposed to the gas being detected, is continuously oxidized which causes a resistance increase at the interface of the back electrode and dielectric. The use of tin oxide gas sensors, on the other hand, has required the prior art chemisorption based gas sensors to be operated at temperatures considerably above room temperature, such as 350°-400° C. The prior art tin oxide and rare earth fluoride amperometric based sensors are also humidity sensitive; the tin oxide is manually painted on a substrate, typically formed as a cylinder.

By utilizing a lanthanum fluoride dielectric, the need for a power consuming heater, as frequently employed in the prior art, is obviated. By energizing the capacitor having a lanthanum fluoride electrolyte dielectric with an AC voltage there is no tendency for impurities to be driven into the bulk material of the dielectric; instead, the impurities remain on the dielectric surface. The magnitude of the AC voltage is sufficient to create oxygen ions from atmospheric oxygen, but is less than the breakdown voltage of the lanthanum fluoride dielectric. There is a large dipole layer field of the lanthanum fluoride that is modulated only during alternate half cycles of the AC voltage, whereby deposited molecules on the surface of the lanthanum fluoride stretch and are easily broken up to generate oxygen ion species. Hence, during alternate half cycles of the AC source, the capacitor has relatively high and low conductivities to cause the detector to be operated in a diode-like mode.

In contrast, in the physisorption process, the resistance and capacitance changes of the second equivalent circuit are insensitive to the voltage applied to the dielectric. There is no chemical reaction between the adsorbent and adsorbate molecules. The physisorbed polar gases cause the space charge thickness to decrease, which is measured by an increase in the second equivalent circuit capacitance, as detected by applying the low, second frequency range to the detector.

Lanthanum fluoride is particularly desirable as the solid electrolyte dielectric because it is capable of detecting a large number of gases over a wide temperature range, including room temperature, i.e., approximately 20° C. or 300° K. For example, oxygen and gases such as as nitric oxide (NO), carbon monoxide (CO) and carbon dioxide ($CO_2$), can be detected with a capacitor having a lanthanum fluoride dielectric supplied with an AC voltage in the range of 0.3–3 volts at a frequency in the range of 0.03–30 Hz. At the lower temperature ranges the influence of humidity on the high water water sensitive lanthanum fluoride can be minimized by covering an inert or catalytic grid on the lanthanum fluoride with a hydrophilic salt or by covering the lanthanum fluoride surface exposed to the gas with a hydrophobic coating, for example a Teflon membrane. The hydrophilic salt removes water from the lanthanum fluoride dielectric, while the hydrophobic coating prevents the deposition of water on the dielectric. At higher temperatures, i.e., above 100° C., the water vaporizes and the effects thereof on the lanthanum fluoride are a minimum.

In the chemisorption mode, oxygen from the specie desired to be detected is adsorbed on the lanthanum fluoride. Alternatively, a catalytic grid on the lanthanum fluoride changes the number of molecules from the atmosphere which are adsorbed by the lanthanum fluoride as a result of an interaction between the catalytic grid and a reducing gas being sensed. Electrons from the grid on lanthanum fluoride dielectric are transferred to the adsorbed oxygen on the dielectric surface to form a reactive intermediate, for example an oxygen ion ($O^-$). The reactive intermediate oxygen ion reacts with a reducing gas to be detected, such as methane, propane, or carbon butane. The reaction between the reactive intermediate oxygen ion and the reducing gas removes an $O^-$ species from the dielectric surface. The oxidized reducing gas is then desorbed, i.e., expelled from the surface of the lanthanum fluoride dielectric into the atmosphere. This sequence of events occurs in response to the applied AC voltage having an amplitude and frequency which causes the chemisorption reaction to occur. The components of the second equivalent circuit change in value in response to the variation in $O^-$ on the dielectric surface The applied voltage, dielectric ionic conductivity, and the nature of the analyte gas determine when the reactive oxygen species starts to form, e.g., for a lanthanum fluoride dielectric having a certain dopant level, the reactive oxygen species starts to form in response to different voltage magnitudes being applied to the capacitive sensor. The magnitude of the voltage at which the reactive oxygen species starts to form is correlated with the gas species (e.g., $O_2$, $NO_x$, $SO_x$) for species identification. For extrinsically doped lanthanum fluoride, the oxygen ion specie starts to form at a voltage of 0.3 volts AC. If, however, the lanthanum fluoride is intrinsic, the oxygen ion specie starts to form only in response to 3 volts AC being applied across the electrodes of the capacitor including the lanthanum fluoride dielectric.

To optimize the response, the device has a large surface area, whereby a large number of oxygen ions are formed on the lanthanum fluoride surface. Also, it is desirable for the catalytic grid to be formed of a material which is a good oxygen catalyst. The grid is either a fine grid, i.e., one in which gas does not go through the bulk of the grid but only through openings between the grid lines, or a porous grid, i.e., a grid formed of a material which adsorbs the oxygen ions and enables them to be transported to the lanthanum fluoride surface on which the grid is situated.

It is also possible to use a catalytic adsorber film having a large surface area relative to the surface area of the lanthanum fluoride surface that adsorbs the gas molecules. Catalytic adsorber film materials that cause the sensed gas to replace oxygen molecules in the air most effectively can also be used. The catalytic films enable the device to select different species, whereby an array of capacitors with different catalytic films can be energized into the chemisorption mode to detect different gases. In addition, capacitors having several different solid electrolytes, i.e., ionic, dielectrics can be energized into the chemisorption and/or physisorption modes to detect a large number of different gaseous species. If dielectrics other than lanthanum fluoride are employed, it may be necessary to heat them.

In the physisorption mode, no reaction with oxygen is necessary, whereby the device always functions at room temperature. The adsorbed gas molecules modulate the space charge in the lanthanum fluoride, to cause a change in capacitance at the frequency of the low amplitude voltage applied to the capacitor electrodes. The sensitivity of the device is relatively high because the space charge capacitance, an exponential function of the free energies at the surface of the dielectric, is modified by the gas in the physisorption mode. The exponential relationship implies large capacitance changes as a function of gas concentration, to provide the high sensitivity.

To effectively detect the impedance of the capacitor, the voltage magnitude and phase angle of the AC voltage across the monitoring capacitor are determined. To this end, a sampling resistor is connected in series with the capacitor and the voltage across this resistor is monitored. The phase of the voltage across the sampling resistor is compared with the phase of an AC source which drives the network including the sensing capacitor and the sampling resistor. The amplitude and frequency of the source are stepped by a computer-type arrangement to measure physisorption and chemisorption responses over a wide frequency range, such as 0.03–30 Hz.

The phase and voltage across the sampling resistor are detected at each amplitude and frequency position. The sampled phases and voltages are supplied to a computer-type network, where they are compared with previously stored values of voltage and phase for known species and concentrations. The computer correlates the sampled voltages and phases with the previously stored voltages and phases to provide indications of the particular detected specie and the concentration thereof.

Alternatively, the AC source has a single frequency, such as 1 Hz, and is stepped through a range of amplitudes to measure the chemisorption and physisorption reactions at the capacitor dielectric. For the amplitudes which induce chemisorption reactions, the phase across the sampling resistor is detected for the fundamental and higher odd harmonics. The fundamental and odd harmonic phase responses are detected and compared with previously stored values therefor for the different species to be detected by the instrument. The species identification is used to address a memory which is responsive to the detected voltage across the sampling resistor, to provide an indication of the concentration of the detected specie.

We have theoretically determined that the variable amplitude, harmonic detection technique is particularly advantageous to detect a low concentration of one gas in the presence of high concentrations of other gases. For example, if a gas sample contains oxygen and carbon dioxide constituents, the oxygen and carbon dioxide constituents can be detected separately by the harmonic, chemisorption technique because the non-linear response is initiated for lower voltages in the presence of oxygen than in the presence of carbon dioxide. Hence, with oxygen on the dielectric surface significant harmonics are produced in the chemisorption mode at a relatively low voltage; harmonics are produced only at higher voltages in the presence of carbon dioxide gas. If carbon monoxide is a further constituent of the analyzed gas, the chemisorption diode action occurs for an intermediate voltage, i.e., a voltage between the voltage which causes diode action for oxygen and diode action for carbon dioxide.

A similar arrangement utilizing an array of plural capacitive detectors, some of which have different solid, electrolyte dielectrics and/or catalysts can be employed. The array detectors are responsive to an AC source and can be operated in the chemisorption and/or physisorption modes. The voltage and phase across each of the dielectrics are detected and supplied to a computer network, for correlation with previously stored responses of the capacitor array to previously detected species and concentrations.

To detect relative humidity and temperature, a capacitor preferably having a lanthanum fluoride dielectric is responsive to a low frequency source which measures the physisorption reaction between the lanthanum fluoride and the water molecules being detected. The lanthanum fluoride dielectric is also responsive to a much higher frequency AC, e.g. 1 kHz, that produces a response only indicative of temperature. The voltage and phase across a sampling resistor in response to both of these AC frequencies are detected. A computer-type network responds to the detected voltage and phase in response to the high frequency signal to detect temperature. The computer also responds to the detected voltage and phase for the low frequency excitation to derive a response that is modified by the temperature indication to provide an accurate indication of relative humidity that is independent of temperature.

Lanthanum fluoride is particulary desirable as the dielectric because it is chemically stable, has a high melting point and is nearly a superionic conductor. Even though lanthanum fluoride has a very high melting point, approximately 1500° C., fluorine ions move through the material rapidly at room temperature. Because it is an ionic material, the electron and hole mobilities thereof are relatively low, making it an excellent insulator to electron flow. There is a difference of more than 0.25 electron volts between the Helmholtz free-energy for $La^{3+}$ and $F^-$ ions going from the bulk interior of the material to the surface thereof. Thereby, dipole layers exist at all surfaces, resulting in large surface electric fields. The bulk dielectric constant is 14, a relatively large number for an electrolyte dielectric. However, because the bulk material has dipole layers and ionic conductivity, capacitors made from lanthanum fluoride typically have much larger capacitance values than the geometrically determined value.

It has been found that if a grid-shaped electrode on a lanthanum fluoride surface is exposed to a reducing gas while a ramp voltage is applied across the lanthanum fluoride, the resulting current exhibits steps at voltages that are characteristic of different gases. Each step amplitude is a measure of the partial pressure of the gas causing the step. In addition, the space charge distribution under the electrode is modified each time a step occurs. The present invention uses this phenomenon in the variable amplitude AC embodiments.

It has been found that the application of a DC current to a gas detector formed as a capacitor having a lanthanum fluoride electrolyte dielectric has a slow response time. The sensitivity of lanthanum fluoride capacitive gas detectors decreases by a factor of approximately 50, apparently because the space charge layer at the lanthanum fluoride surface disappears, causing the bulk resistivity of the lanthanum fluoride to be modified. Although the bulk resistivity modifications that accumulate after prolonged exposure to a reducing gas and a DC voltage are reversible, the lanthanum fluoride space charge never returns to the original condition thereof. Apparently, the only way the space charge reduction can occur is if the surface is electrochemically modified in such a way that the free energy difference between the surface thermal excitation of $La^{3+}$ and $F^-$ ions is significantly reduced. The electrochemical modification is performed in the present invention by energizing the capacitor including the lanthanum fluoride dielectric with an AC voltage in the stated range for chemisorption operation. As the free energy difference changes in response to the AC voltage, the space charge thickness is influenced strongly. The space charge thickness is effectively measured by monitoring the voltage and phase across the sampling resistor in series with the capacitor. Because DC voltages are not applied to drive surface produced products into the bulk semiconductor dielectric, aging and hysteresis are reduced.

The above and still further objects, features and advantages of the present invention will become apparent upon consideration of the following detailed description of several specific embodiments thereof, especially when taken in conjunction with the accompanying drawings.

BRIEF DESCRIPTION OF DRAWINGS

FIG. 5 is an equivalent circuit diagram of the devices illustrated in FIGS. 1-4, when operated in the physisorption mode;

FIG. 6 is a partial circuit and partial block diagram of a first embodiment of the present invention wherein a gas detecting capacitor operated in the physisorption and chemisorption modes is responsive to a variable amplitude and variable frequency oscillator;

FIG. 7 is a partial circuit and partial block diagram of a second embodiment of the invention wherein a gas detecting capacitor operated in the physisorption and chemisorption modes is responsive to a variable amplitude and single frequency source, with harmonic frequencies being detected for the chemisorption mode;

BEST MODE FOR CARRYING OUT THE INVENTION

Figure 1:
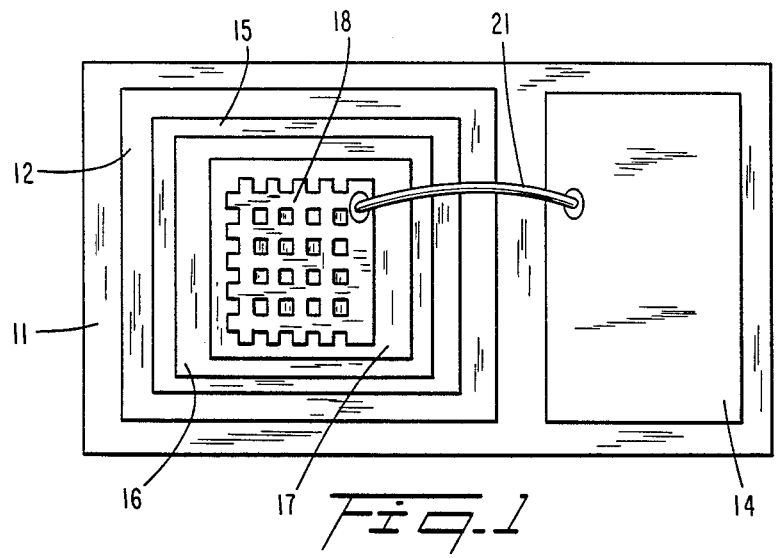
FIG. 1 is a top view of a thin film detector in accordance with one aspect of the present invention.
Figure 2:
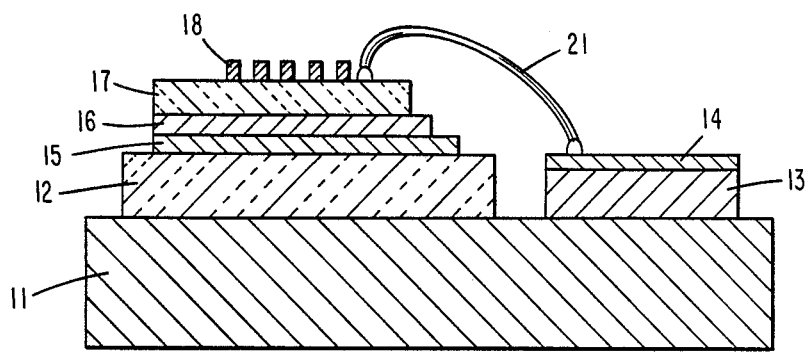
FIG. 2 is a side view of the detector illustrated in FIG. 1.

Reference is now made to FIGS. 1 and 2 of the drawing wherein there is illustrated a preferred embodiment of a gas sensing or detecting capacitor in accordance with a first embodiment of the invention. The gas detecting capacitor is mounted on a copper substrate or support 11 that serves as an electrode. On support 11 are respectively attached silicon chip 12 and glass, electric insulator plate 13. Silicon chip 12 is degenerate, having high electric conductivity. Gold layer 14, deposited as an electrode on glass plate 13, is electrically insulated from copper substrate 11. Degenerate silicon chip 12 provides a very flat surface on which to deposit chromium thin film layer 15, on which is deposited copper thin film layer 16. Chromium layer 15 is necessary to provide adherence of copper layer 16. Deposited on copper layer 16 is solid ionic, i.e., electrolyte, thin film dielectric layer 17, preferably the rare earth fluoride lanthanum fluoride ($LaF_3$) having a thickness of 1000–2000 Angstroms, for room temperature gas detection purposes. Although lanthanum fluoride is particularly advantageous as pointed out supra, it is to be understood that other ionic dielectrics, particularly other rare earth fluorides, can be used as layer 17. Copper layer 16 provides a thermal expansion match to lanthanum fluoride layer 17, and is thick enough to mechanically isolate the lanthanum fluoride layer from silicon chip 12.

Thin film metal grid 18 is formed on the upper surface of dielectric layer 17. Grid 18 includes interstices with sufficient area to enable a relatively large percentage, such as 50% or more, of the top surface of dielectric layer 17 to be exposed to a ambient gas to be detected by the device. Grid 18 may be an inert metal, preferably gold, or it may be a catalytic metal, such as pallidium. Alternatively, grid 18 can be replaced by a catalytic porous metal layer which absorbs molecules from the gas being detected. The adsorbed molecules migrate through catalytic porous metal layer and are adsorbed on the surface of dielectric layer 17.

Grid 18 or the porous metal layer on dielectric layer 17 is connected to gold layer 14 by gold lead 21 to form a first electrode of the capacitor. Copper support 11 forms a second electrode of the capacitor. The electrodes including support 11 and layer 14 are respectively designated as the anode and cathode of the device. In response to a sufficiently high positive voltage being applied to support 11 relative to layer 14, significant current flows from support 11 through chip 12 and layers 15 and 16 to layer 17 which functions as a forward biased semiconductor. From layer 17 the current flows to grid 18 (or the equivalent porous layer) and lead 21 to layer 14. The impedance from support 11 through dielectric glass plate 13 to layer 14 is sufficiently high to be considered an open circuit. In contrast, if a lower positive voltage or any negative voltage which does not cause breakdown of the ionic dielectric or of glass plate 13 is applied to support 11 relative to layer 14, the path including chip 12 and series layers 15, 16 and 17 to grid 18 is back biased and functions only as a dielectric. The diode action is accompanied by the chemisorption mode of device operation whereby a chemical reaction occurs between gases on the exposed dielectric face to affect the electric impedance of layer 17.

Figure 3:
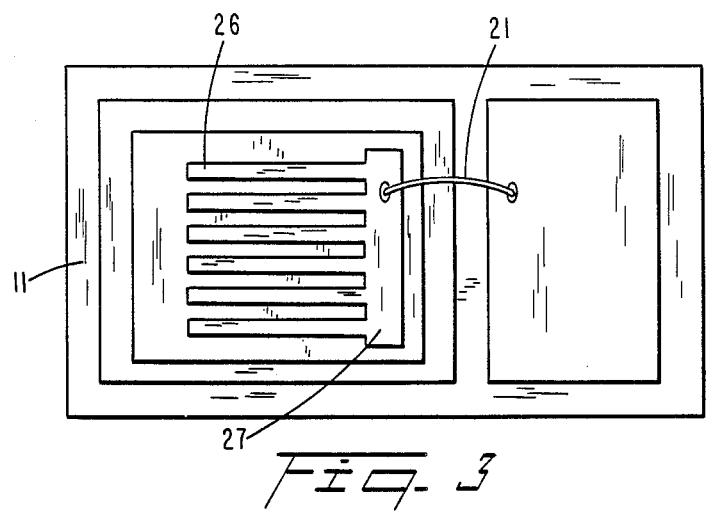
FIG. 3 is a top view of a single crystal detector in accordance with a second embodiment of the invention.
Figure 4:
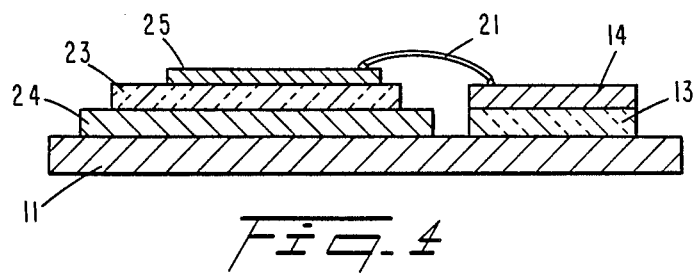
FIG. 4 is a side view of the detector illustrated in FIG. 3.

In a second embodiment of the invention, as illustrated in FIGS. 3 and 4, thin film ionic, dielectric layer 17 is replaced by single crystal dielectric slice 23, preferably lanthanum fluoride, typically having a thickness of about 200 micrometers. Lanthanum fluoride slice 23 is supported by silver layer 24, which is deposited on copper support or substrate 11. Silver layer 24 is used in lieu of the silicon and chromium layers of FIGS. 1 and 2 because single crystal lanthanum fluoride slice 23 is self-supporting and does not require the support functions provided by the silicon chip. Deposited on the exposed surface of dielectric crystal slice 23 is electrode 25, which can be formed as a number of parallel fingers 26, extending from elongated arm 27, or which can formed as a grid, as illustrated in FIGS. 1 and 2, or as a porous gas adsorbing layer (not illustrated). Layer 25 can be formed of gold, or a metal catalyst that is a function of the gas being detected. Glass plate 13 and gold layer 14 are deposited on copper support 11 in spaced relationship to silver layer 24 in the embodiment of FIGS. 3 and 4, in a manner similar to deposition of glass plate 13 and layer 14 on support 11 in the embodiment of FIGS. 1 and 2.

Figure 2A:
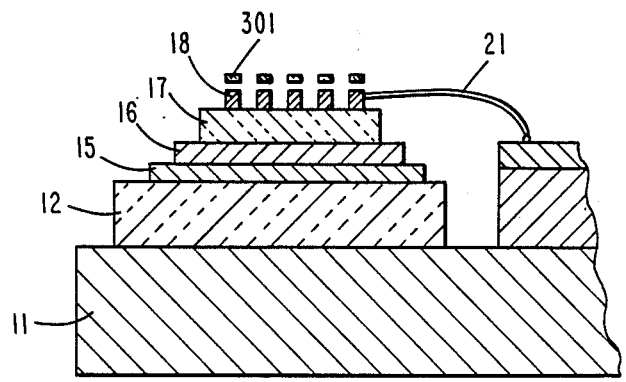
FIG. 2a is a side view of a modification of the detector illustrated in FIGS. 1 and 2.
Figure 4A:
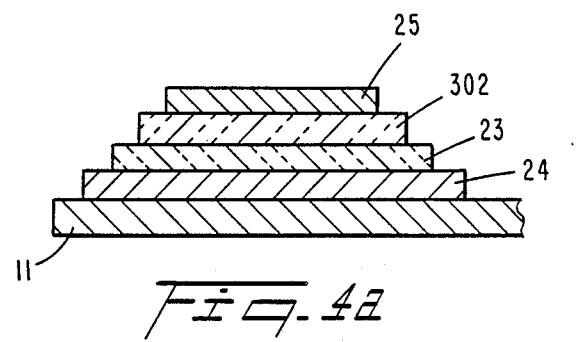
FIG. 4a is a side view of a modification of the detector illustrated in FIGS. 3 and 4.

To detect certain gases, such as oxygen, with greater accuracy, it is preferable for the ionic dielectric to be unresponsive to ambient moisture. Because lanthanum fluoride is highly water sensitive it is important, in the detection of certain species, to prevent water vapor from being incident thereon. To this end, a thin film hydrophilic salt layer 301, FIG. 2a, suspended slightly above the upper, exposed surface of grid 18 by dielectric posts (not shown) that extend upwardly from dielectric layer 17. Hydrophilic layer 301 absorbs water molecules which otherwise might be incident on the lanthanum fluoride dielectric so that the water molecules do not have an affect on the impedance of the dielectric. Alternatively, hydrophobic layer 302, preferably a Teflon coat, which repels water molecules is deposited on the lanthanum fluoride (FIG. 4a). Because layer 302 repels water molecules in the vicinity of the lanthanum fluoride dielectric, the dielectric impedance is not affected by them. Thus, the hydropholic salt layer 301 and the hydrophobic coating 302 both minimize the influence of water vapor, i.e., humidity, on the action of the detector. The hydropholic salt attracts water molecules in the air and prevents them from reaching the lanthanum fluoride. The hydrophobic coating on the lanthanum fluoride surface repels water molecules in the air, to prevent them from reacting with the lanthanum fluoride.

The mechanisms involved in the operation of the devices illustrated in FIGS. 1, 2, 3, and 4 are the same. Chemisorption and physisorption operation can be made to occur in both embodiments. In physisorption, AC or DC voltage having an amplitude only sufficient to probe for van der Waal's forces (typically between 1 and 100 millivolts) are applied between the electrodes comprising support plate 11 and film 14. In chemisorption in accordance with the invention, a higher voltage, which is always AC, is applied between the electrodes; the voltage amplitude is sufficient to form $O^-$.

Silver layer 24, FIG. 3, is operated as an anode, while layer 26 is operated as a cathode. The voltage at which current starts to flow depends on the doping level of ionic dielectric layer 17 or crystal 23, as well as the specie of gas which is incident on the dielectric and the material of the dielectric layer. For extrinsically doped and intrinsic lanthanum fluoride dielectrics, current onset respectively begins for anode forward bias voltages of approximately 0.03 and 3.0 volts AC RMS for a particular gas specie. The peak voltage between the capacitor electrodes must not exceed the dielectric breakdown voltage; for intrinsic lanthanum fluoride, the breakdown voltage is approximately 5 volts for thicknesses of layer 17 and crystal 23 that exceed a few times the surface dipole layer thickness.

In the chemisorption mode, the voltage at which reaction begins determines what specie or species of gases are incident on the lanthanum fluoride dielectric. The magnitude of the current flow once the reaction has been initiated indicates the amount of gas, i.e., the concentration of a particular gas. As described, infra, the gas species and concentration are determined in accordance with one aspect of the present invention by applying AC excitation voltages to capacitors of the type illustrated in FIGS. 1-4. To detect the gas species, the AC amplitude of the voltage required for the onset of sensing action is detected. The AC excitation can be from a single frequency variable amplitude AC source with detection of the fundamental and odd harmonics, or from a variable frequency, variable amplitude AC source. Aging effects which occur in DC operation do not occur with AC excitation because molecules of the analyzed species are not accumulated in the sample. The frequency of the AC source may be sufficiently low to enable the adsorbtion and desorbtion processes to occur.

To consider the chemisorption process, assume that is desired to detect methane ($CH_4$) in an atmospheric ambient condition. An atmospheric ambient condition includes numerous oxygen molecules which are incident on the exposed lanthanum fluoride surface of layer 17 or crystal 23. When anode 16 is forward biased relative to cathode 18 during the adsorbtion process, oxygen molecules incident on the exposed dielectric surface are converted into oxygen ions. Oxygen ions on the exposed ionic dielectric surface react with the methane in the atmosphere to form methyl alcohol ($CH_3OH$). Because the oxygen reacts with the methane to form methyl alcohol, there are fewer oxygen ions available to migrate into the lanthanum fluoride lattice, whereby the forward bias necessary to achieve a predetermined current level is higher than the forward bias necessary to achieve the same current without the presence of methane in air. Detecting the voltage at which the reaction begins indicates that methane is present. Similar mechanisms occur at different voltages for carbon monoxide, carbon dioxide, silicon dioxide, butane, propane and other reducing gases. Detecting the AC voltage which initiates the onset of diode action enables each of these gases to be detected. The reactions occur at relatively low temperatures and above, for example, at room temperatures and above; detection is typically possible from about 18° C. to at least about 400° C. Concentration of the detected species is determined by monitoring the AC current which flows at the characteristic voltage required for the onset of reaction.

If the electrode formed by grid 18 or the equivalent porous layer overlaying the ionic dielectric is formed as a catalyst, the catalyst is selected from the following sets of materials for detection of the indicated gases: for methane detection, the catalyst is any of palladium (Pd), zinc oxide (ZnO), ferric oxide ($Fe_2O_3$) or tin dioxide ($SnO_2$); for oxygen, the catalyst is any of iridium dioxide ($IrO_2$), cobalt-phthalocyanine or iron-phthalocyanine; for hydrogen sulfide ($H_2S$), the catalyst is a metal sulfide, preferably CdS; for $H_2$, the catalyst is palladium. If grid 18 or grid 25 is formed of cobalt-phthalocyanine or iron-phthalocyanine, there is a lower potential required to initiate sensing action and a faster response is attained. It is desirable to lower the required potential required for sensing action to assure that the dielectric break down voltage is not exceeded.

An equivalent circuit modeling the physisorption mechanisms involved in the devices illustrated in FIGS. 1, 2 and 3, 4 is illustrated in FIG. 5. The physisorption mode is particularly advantageous for sensing of polar molecules, such as water. The oxygen in each water molecule is very electro-negative, drawing hydrogen electrons in the molecule toward it. Thus, there is a partial negative charge on the oxygen in each water molecule and a partial positive charge on the hydrogen in each water molecule. The ionic dielectric layer 17 or single crystal slice 23 preferentially adsorbs molecules with a dipole moment. The adsorbed species on the surface of the lanthanum fluoride modify the lanthanum fluoride space charge, causing changes in the AC impedance parameters associated with the lanthanum trifluoride gas interface. It has been found that the physisorption mode is particularly advantageous for sensing of humidity and isopropanol; in addition, a small physisorption effect has been detected in capacitors having lanthanum trifluoride dielectrics exposed to carbon monoxide.

Both of the capacitors illustrated in FIGS. 1, 2 or 3, 4 include a bulk material dielectric, represented as capacitor 33, between terminals 34 and 35, FIG. 5. The capacitance of capacitor 34 is that of the bulk material of the lanthanum fluoride having a dielectric constant $\epsilon$, thickness d, and area A, in accordance with:

$$C_0 = \epsilon A / d.$$

In shunt with capacitor 33 is a branch including series resistor 36 and series capacitance 37. The capacitance $C_1$ of capacitor 37 is associated with space charge layers that appear at all surfaces of the lanthanum fluoride dielectric. The space charge results from a free energy difference between an $F^{31}$ ion and an $LaF_2^+$ ion being excited from the bulk material to the surface of the lanthanum fluoride. Lanthanum fluoride has a low activation energy of 0.08 electron volts for a neutral lanthanum fluoride formula unit forming a Schottky defect, i.e., for a neutral lanthanum fluoride formula unit excited from the bulk to the surface. These neutral formula units have an $F^-$ ion excited into them leaving an $(F^-)^+$ hole that acts as a positively charged particle in response to an externally applied electric field. The $F^-$ ion occupying a neutral lanthanum fluoride formula unit volume is less mobile than an $(F^-)^+$ hole since a $LaF_2^+$ ion must hop from an adjacent site into the empty hole, in order for the $F^-$ ion to move. The defect of the neutral formula unit can thus be treated as a $(LaF_2^+)^-$ hole, a negatively charged specie. The $LaF_2^+)^-$ hole preferentially moves to the surface, leaving behind a space charge layer of $(F^-)^+$ holes. These dipole layers are responsible for the capacitance $C_1$ of capacitor 37 which can be symbolically written as $C_1 = \epsilon_A/d_1$, where $d_1$ is the total effective thickness of the two space charge layers on either side of the lanthanum fluoride dielectric. The space charge layer thickness $d_1$ varies inversely as the square root of the concentration of the $(F^-)^+$ ions.

The value of the resistance of resistor 36 represents the ionic resistance of the lanthanum fluoride layer due to the motion of the $(F^-)^+$ hole across the thickness of the lanthanum fluoride, and can be written $R_1 = \rho d/A$, where $\rho$ is the resistivity of the lanthanum dielectric layer 17 or crystal 23 between the opposite faces thereof.

In shunt with capacitor 37 is a branch including series resistor 38 and capacitor 39, which together represent the effects caused by the motion of the partially mobile ionic species $(LaF_2^+)^-$ under the influence of electric fields remaining after the fast ion motion is completed and thermal driving forces have been exhausted. Charge is stored in the surface states of the lanthanum fluoride layer 17 or crystal 23; the finite response time of the surface states to an external stimulus contributes to the values of resistor 38 and capacitor 39. It is this leg of the circuit, including resistor 38 and capacitor 39, that contains the gas sensitive elements of the device. Thus there is gas sensitivity only when the sensing frequency is low enough so these elements of the circuit respond.

When a step voltage is applied to the capacitor, the effects of resistor 38 and capacitor 39 tend to produce time varying currents that are not simple exponentials. As a consequence, the temporal response of the branch represented as resistor 38 and capacitor 39 is not a simple exponential, and cannot be represented by a finite number of resistor-capacitor circuit elements. Therefore, the portion of the lanthanum fluoride dielectric represented by resistor 38 and capacitor 39 is an actuality a frequency and voltage dependent impedance which is represented as a complex function $Z(\omega)$. The main effects of the complex impedance $Z(\omega)$ can, for many of the purposes under consideration therein, be thought of as frequency dependent resistor 38 and capacitor 39 variables.

It can be shown that the value of capacitor 39 is much greater than that of capacitor 37 and corresponds to a vary thin space charge thickness, perhaps only a few atomic layers thick in some cases. The main gas response of detectors operated in the physisorption mode is associated with changes in the values of the complex impedance in the branch including resistor 38 and capacitor 39. The largest fields occur at the negative electrode, whereby the maximum gas response occurs at the interface between the exposed upper surface of the lanthanum fluoride and grid 18 or layer 23.

Consider the situation of the device schematically illustrated in FIG. 5 for a high frequency region (an applied voltage having a frequency in excess of 6 kHz), a mid-range frequency (where the applied frequency is between 30 Hz and 6 kHz), and a low frequency region (where the frequency is less than 30 Hz). These characteristic frequencies are dependent upon both sample thickness and doping and can therefore be adjusted in the sample preparation by changing the thickness and doping parameters. In all three of these assumptions, the applied voltage is no greater than 100 mv, whereby van der Waal's forces are the forces of attraction between the lanthanum fluoride surface layers and the molecules incident thereon and there is no diode action due to chemisorption.

In the high frequency region, the principle impedance is due to the bulk capacitance of capacitor 33 between terminals 34 and 35. The resistance of resistor 36 and the impedance of capacitor 37 relative to the impedance of capacitor 33 at frequencies above 6 kHz are such that only the bulk capacitance (as represented by capacitor 33) has any effect on the impedance of the device. In the intermediate range, the response is determined mainly by resistor 36 and capacitor 37. The impedance of the branch including resistor 38 and capacitor 39 shunting capacitor 37 is so large in this frequency range that it does not have any appreciable effect on the impedance between terminals 34 and 35. The bulk impedance of capacitor 33 at these frequencies can be made relatively constant over the entire frequency range from 30 Hz to 6 kHz, so that the bulk capacitance represented by capacitor 33 does not significantly alter the impedance between terminals 34 and 35. In the low frequency range below 30 Hz, the response between terminals 34 and 35 is dominated by the complex impedance $Z(\omega)$ in the branch including resistor 38 and capacitor 39. The time constant, $T_1 = R_1 C_1$ of resistor 36 and capacitor 37, determines the frequency at which the low frequency and intermediate frequency effects become dominant. The time constant depends on the thickness d of the dielectric. Thus, for relatively thick dielectric layers or slices, $T_1$ may be shifted until the intermediate and low frequency responses are not particularly separated.

Figure 8:
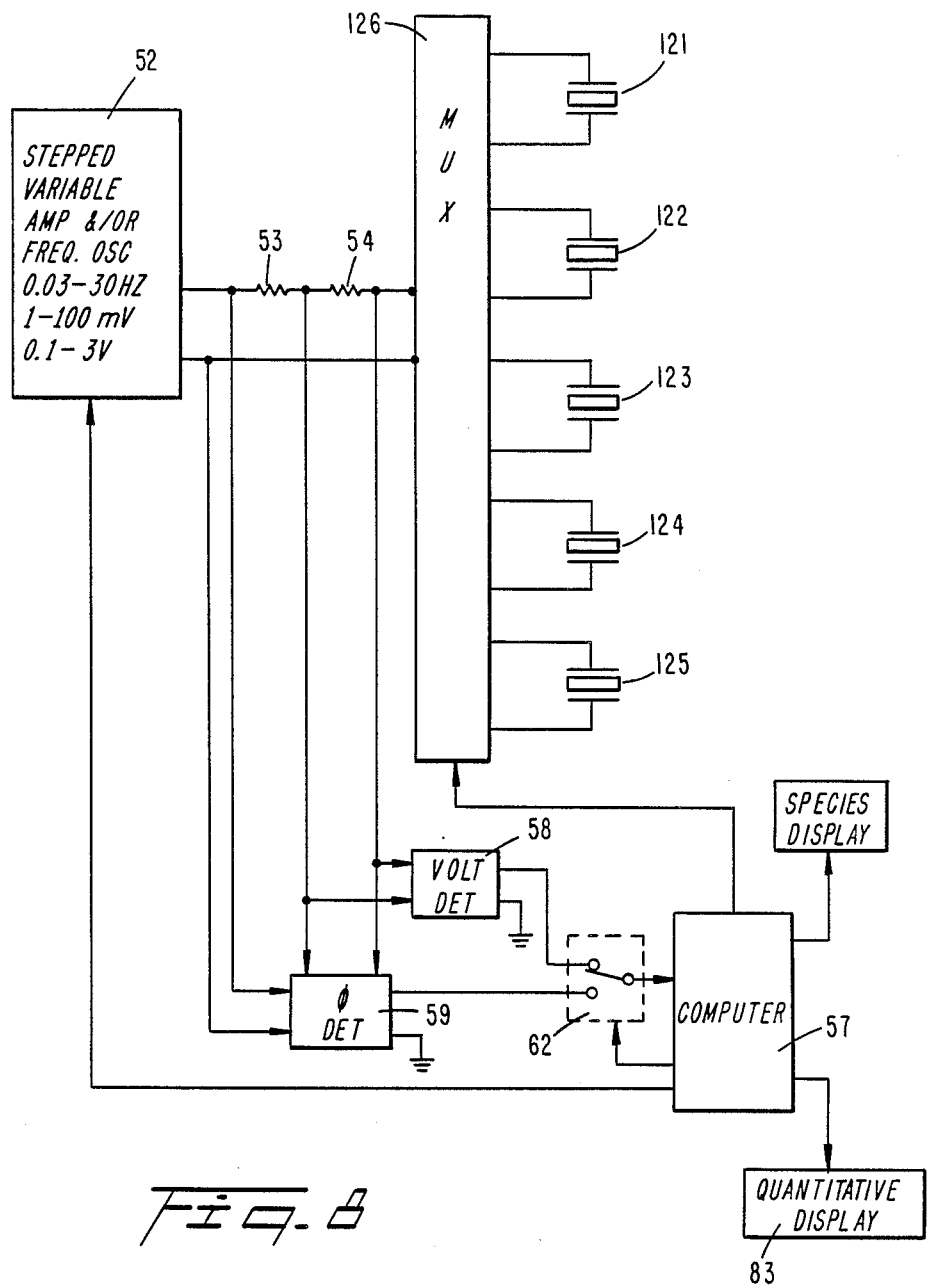
FIG. 8 is a partial circuit and partial block diagram of still another embodiment of the invention wherein plural detetors, each having different responses to different gases are energized into the chemisorption and physisorption modes by a variable amplitude and variable frequency source.

Three different embodiments of AC multiple gas specie sensors are illustrated in FIGS. 6–8. In the embodiments of FIGS. 6–8, the AC RMS voltage across a capacitive sensor is detected and a phase comparison is made between an AC energization voltage supplied to a circuit including the sensor and the current flowing through the sensor. The voltage and phase measurements effectively enable the complex impedance of the sensor to be determined. Computer techniques are utilized to correlate the response from the detector or detectors with previously stored responses to enable the specie to be identified and the concentration thereof to be determined. Physisorption and chemisorption techniques are employed in all of these embodiments.

In the embodiment of FIG. 6, capacitor 51, having a lanthanum fluoride dielectric, is connected to a variable amplitude and variable frequency oscillator 52 by way of current sampling resistor 54. The impedance of resistor 54 is relatively low compared to the impedance of capacitor 51, so that the voltage developed across resistor 54 is a replica of the current waveform developed in capacitor 51. The magnitude of the voltage across resistor 54 is directly proportional to the current amplitude flowing in capacitor 51. The phase of the voltage across resistor 54 relative to the phase at output terminals 53 of oscillator 52 indicates the phase angle between the voltage applied to capacitor 51 and the current flowing through the capacitor.

Oscillator 52 has a variable step amplitude and variable step frequency output of sinusoidal or square wave shape. The amplitude of oscillator 52 is stepped through a sequence of values so that the AC RMS voltage applied across the electrodes of capacitor 51 is either in the range of 1–100 mv for physisorption operation, or 0.1 to 3.0 volts for chemisorption operation. The frequency of source 52 is stepped through a multi-decade range from 0.03 to 30 Hz. The upper frequency of this range is set for the reasons described in connection with the description of FIG. 5. Oscillators of the described type are well known and frequently employed in network analyzers. While it is theoretically possible to operate oscillator 52 at a frequency less than 0.03 Hz, the practical ramifications of generating and detecting such a low frequency source generally preclude such low frequency operation. It is important that an AC excitation voltage be applied to capacitor 51 and that no DC voltage be applied across the capacitor electrodes, for the reasons discussed supra.

Oscillator 52 includes a control input terminal 55, responsive to the output of timer 56, included in computer-type network 57. Oscillator 52 is programmed to respond to each signal supplied to control input 55 thereof by timer 56 to derive an AC output having a predetermined frequency and amplitude. The oscillator amplitude is maintained constant while the oscillator frequency runs through a gamut of frequencies in response to a series of outputs from timer 56. When the highest output frequency of oscillator 52 for a particular amplitude has been reached, the amplitude of the oscillator output is incremented to a higher level and the gamut of frequencies is again sequenced.

Capacitor 51 responds to each amplitude and frequency output of oscillator 52 as a function of the gases incident on the capacitor which determine the complex impedance of the capacitor. The capacitance and resistance values of capacitor 51 affect the voltage across resistor 54 and the phase of the voltage across resistor 54 relative to the phase of the AC voltage at output terminals 53 of oscillator 52. The voltage developed across resistor 54 is monitored by AC voltage detector 58, which derives a DC output indicative of the RMS voltage across resistor 54. The difference in phase between the voltage across resistor 54 and the output terminals 53 of oscillator 52 is monitored by phase detector 59 which derives a DC voltage having an amplitude indicative of the phase difference. The DC outputs of detectors 58 and 59 are applied to analog-to-digital converter 61, part of computer network 57, via electronic switch 62. Analog-to-digital converter 61 derives a parallel multi-bit output that is coupled via electronic switch 63 to random access memory (RAM) 66 having the usual write enable input, read enable input, address input and data bus.

Switches 62 and 63, as well as memory 66 are controlled by outputs of timer 56 so that just prior to completion of each amplitude and frequency position of oscillator 52 different addresses of the memory are loaded with multi-bit binary signals indicative of the amplitudes of the outputs of detectors 58 and 59. Timer 56 controls switches 62 and 63 and memory 66 so that the output of detector 58 is coupled to the input of converter 61 while the output of the converter is coupled to a first designated address of memory 66 immediately prior to termination of a particular amplitude and frequency position of oscillator 52. Then, while oscillator 52 continues to derive a single output, timer 56 activates switches 62 and 63 and memory 66 so that the output of phase detector 59 is coupled to the input of converter 61 and the multi-bit output of the converter is coupled to a second designated memory address.

As oscillator 52 is being stepped through a gamut of frequencies for a particular amplitude, the amplitude and phase indicating signals derived from converter 61 are loaded into random access memory 66. Timer 56 controls the addresses in RAM 66 into which the data from converter 61 are stored. After the data for the gamut of frequencies at one amplitude of source 52 have been stored sequentially in different addresses of RAM 66, the voltage and phase derived from capacitor 51 for a second amplitude of source 52 are loaded into a second sequence of addresses of RAM 66 under the control of timer 56. Thereby, when timer 56 has stepped oscillator 52 through all of the amplitude and frequency positions of the oscillator, RAM 66 stores an array of data representing the outputs of detectors 58 and 59 at each amplitude and frequency position of the oscillator. The system is then ready to determine what specie or species were incident on capacitor 51 and the concentration thereof, i.e., to provide information as to the qualitative and quantitative nature of the gases incident on detector 51.

To these ends, the signals stored in random access memory 66 are compared with previously stored signals in read-only memory 67 having the usual address and read enable inputs and a multi-bit data output. The signals in read-only memory 67 represent the phase angle outputs of detector 59 for known species of gases incident on detector 51 for each amplitude and frequency position of oscillator 52. Prior to installation of the device, the data in read-only memory 67 are accumulated for each gas which can be detected by detector 51. These phase angle indications are stored in read-only memory 67 when the apparatus is manufactured. Each species capable of detection by detector 51 has a unique binary pattern representing the phase angle at each amplitude and frequency position of oscillator 52.

The phase angle indications stored in read-only memory 67 are compared with the monitored phase angle indications stored in random access memory 66 after a complete sequence of amplitude and frequency positions of oscillator 52 has been completed. The comparison is made for all amplitude and frequency positions of oscillator 52. To this end, timer 56 controls read out of read-only memory 67 so the memory sequentially supplies plural multi-bit binary signals to bus 68; one signal is supplied for each of the possible species to be detected by detector 51. The signals on buses 68 are correlated with the signal stored in random access memory 66 for the output of phase detector 59 for each amplitude and frequency position of oscillator 52, as coupled as a multi-bit signal to bus 69. The signals on buses 68 and the signal on bus 69 are correlated to determine the closest similarity between the signals on buses 68 and the signal on bus 69. A test is then made to determine if the similarity is great enough to provide an identification of any gas.

The correlations are determined by providing a number of Tchebycheff distance calculators, equal to the number of gases and combinations of gases that detector 51 is designed to detect in the particular environment where it is located. Tchebycheff distance calculators 71 are all driven in parallel by phase indicating output signals derived by random access memory 66 when timer 56 enables the RAM. Each of the Tchebycheff calculators 71 includes a buffer memory for storing a different multi-bit data output 68 of ROM 67 indicative of the phase angle expected to be derived from phase detector 59 for each specie and combination of species to be detected. Read-out of ROM 67 to Tchebycheff distance calculators 71 is under the control of timer 56 immediately prior to the timer controlling when the Tchebycheff calculations are to be performed. Alternatively, each of calculators 71 includes a register for permanently storing the signals representing the phase angles for the different species and specie combination and ROM 67 is eliminated. Since detector 51 is usually designed to detect plural gases, the phase angle values for all of the different combinations and permutations of the gases to be detected by the detector are stored in ROM 67 or registers in Tchebycheff distance calculators 71.

Tchebycheff distance calculators 71 provide a measure of the similarity of the signals supplied thereto on buses 68 and 69. If the signals on buses 68 and 69 supplied to a particular Tchebycheff distance calculator are identical, there is a zero output of that Tchebycheff distance calculator. As the similarity of the signals supplied by buses 68 and 69 to a particular Tchebycheff distance calculator decreases, the amplitude of the multi-bit output of the particular distance calculator increases. Each of calculators 71 includes a buffer output memory for storing the distance calculated thereby.

After all of the Tchebycheff distances have been determined by calculators 71 the signals in the output buffer memories of the calculators are supplied in sequence to comparator 72 by way of multiplexer 73, controlled by timer 56. Comparator 72 is also responsive to multi-bit signals from registers 74, one of which is provided for each of the gas species and combinations of the species to be detected by detector 51. Registers 74 store signals representing values for the maximum Tchebycheff distance calculated by each of calculators 71 for identification of each gas species and combinations of species to be detected by detector 51. The signals in registers 74 are coupled to comparator 72 by way of multiplexer 75 in synchronism with the coupling of output signals of calculators 61 by multiplexer 73 to comparator 72.

Comparator 72 responds to the input signals thereof to determine if the Tchebycheff distance indicating signal derived by each of calculators 71 is equal to or less than a maximum acceptable Tchebycheff distance stored in each of registers 74. In response to comparator 72 indicating that a particular gas specie or combination of species has a Tchebycheff distance less than or equal to the maximum Tchebycheff distance for that particular specie or combination of species a binary signal indicative of the specie or specie combination is gated from ROM 67 into buffer memory 76 by way of multiplexer 78 that is enabled by the output of comparator 72; multiplexer 78 is sequenced simultaneously and synchronously with multiplexers 73 and 75 so that signals for the same species and specie combinations are continuously coupled to comparator 72 and buffer 76. Buffer memory 76 stores a binary signal indicative of a particular specie or specie combination that has been identified as being incident on detector 51. The binary signal(s) stored in buffer memory 76 is supplied to species digital display 77, which includes a memory so that it can respond to plural different outputs of buffer memory 76 and repeatedly display in sequence alpha indications of the gas species and specie combinations.

The specie indicating signal(s) stored in buffer memory 76 are supplied to an address input of read-only memory 81, also responsive to the multi-bit data output of random access memory 66 on bus 82. When the specie indicating signal(s) from memory 76 is supplied to ROM 66, timer 56 addresses RAM 66 so the RAM output signal represents the amplitudes of the output of voltage detector 58 for all amplitude and frequency positions of oscillator 52. ROM 81 is basically a two input table lookup memory that correlates all of the amplitude outputs of voltage detector 58 for each of the amplitude and frequency positions of oscillator 52 with a particular amplitude, i.e., concentration, for the specie or species combinations indicated by buffer 76. In response to the inputs to ROM 81 on lead 82 and from buffer 76, the ROM derives a multi-bit output having a value indicative of the gas specie concentration.

Prior to operation of the device, the binary output values of ROM 81 are stored at discrete address positions commensurate with the voltage amplitude output signals on bus 82 and the species indications stored in buffer 76. The concentration indicating output signals of ROM 81 are supplied to buffer 82, which in turn drives quantitative numerical display 83. Display 83, like display 79, includes a memory for storing plural signals from ROM 81 for different species detected by detector 51 during an operating sequence of oscillator 52. The numerical and alpha indications respectively provided by displays 83 and 79 occur simultaneously so that an operator viewing the displays is provided with an indication of concentration simultaneously with an indication of gas specie.

Oscillator 52 derives either sinusoidal or square waves. It has been found, through experimentation, that certain gases are detected with greater sensitivity if a square wave is applied to the electrodes of capacitor 51 than if a sinusoid is applied to the capacitor. This is particularly true for the chemisorption technique in connection with methane detection.

Reference is now made to FIG. 7 of the drawing wherein detecting capacitor 51 is connected to stepped variable amplitude and single frequency oscillator 91 by resistor 54 in the same manner that capacitor 51 is connected to oscillator 52 by resistor 54 in the embodiment of FIG. 6. Oscillator 91 is operated at a single frequency, such as 1 Hz, and is stepped in amplitude so that RMS AC voltages of 1-100 mv are applied across the electrodes of capacitor 51 to provide only physisorption operation. The amplitude of oscillator 91 is stepped so that RMS AC voltages in the range from 0.1 to 3 volts are applied across the electrodes of capacitor 51 to provide chemisorption operation. Voltage detector 58 and phase detector 59 are connected to resistor 54 and across the output of oscillator 91 in the same manner that voltage detector 58 and phase detector 59 are connected across resistor 54 and oscillator 52 in the embodiment of FIG. 6.

An important distinction between the embodiment of FIG. 7 relative to that of FIG. 6, is that in FIG. 7 phase detection is provided for odd harmonics of the voltage developed across sampling resistor 54. The odd harmonics are generated by the diode like action of detector 51 with increasing voltages of oscillator 91 in the chemisorption mode. As discussed supra, in the chemisorption mode assymetric response during opposite half cycles of an AC source occur, i.e., there is diode like action. The diode like action of detector 51 occurs for different gases as the AC voltage across the detector reaches different amplitudes. For the physisorption mode and for chemisorption excitation voltages less than the voltage which causes the diode action of detector 31, there are no odd harmonics of the 1 Hz output of oscillator 91 across resistor 54. When the amplitude of oscillator 91 reaches a sufficiently high value to initiate diode action of detector 51, odd harmonics are produced across resistor 54. The amplitude of the odd harmonics provides a measure of the concentration of the gas which initiated the diode action of detector 51. Gas species are identified by monitoring the voltage causing step changes of the odd harmonics generated across resistor 54 by comparing the phases of the odd harmonics across resistor 54 with reference phases of the odd harmonics.

To these ends, the voltage across resistor 54 is supplied in parallel to $N-1/2$ harmonic phase detectors 92 and $N-1/2$ harmonic voltage detectors 93, where N is the number of the highest odd harmonic to be detected for amplitude and phase. Harmonic phase detectors 92 are also responsive the output of harmonic oscillator 94, in turn responsive to the output of oscillator 91 to generate $N-1/2$ odd harmonics ranging from the third harmonic to the Nth harmonic. The harmonics derived by harmonic oscillator 94 are synchronized so that the zero crossings of the harmonic outputs of oscillator 94 occur in time locked relationship with zero crossings of the output of oscillator 91 applied to the network including capacitor 51.

Harmonic phase detectors 92 respond to the harmonics of the voltage across resistor 54 and the output of oscillator 94 to derive DC voltages indicative of the phase relationship of the harmonics generated across resistor 54 and the outputs of harmonic oscillator 94. If there are no harmonics generated across resistor 54 at a frequency corresponding to the frequency of a harmonic phase detector, as coupled to a particular harmonic phase detector by harmonic oscillator 94, the harmonic phase detector derives a zero output. If the voltage across resistor 54 has a significant amplitude at the harmonic associated with a particular harmonic phase detector 92, the harmonic phase detector associated with that frequency derives a DC output having an amplitude indicative of the phase angle of the harmonic across resistor 54 and the corresponding harmonic supplied by oscillator 94 to detector 92. For example, if the third harmonic across resistor 54 is displaced by 45 degrees from the third harmonic supplied by oscillator 94 to the third harmonic phase detector, the third harmonic phase detector derives a DC output that is one-half of the maximum output that can be derived by the third harmonic phase detector.

The amplitudes of the odd harmonics generated across resistor 54 are detected by $N-1/2$ parallel voltage detector networks, each of which includes a bandpass filter 294 responsive to the output across resistor 54. Each of filters 294 drives a separate AC voltage detector 95 that derives a DC voltage directly proportional to the RMS AC voltage applied to the detector. Each of filters 94 is tuned to a different odd harmonic of the 1 Hz signal derived by oscillator 91. Thus, to derive an indication of the amplitude of the third harmonic across resistor 54, the first bandpass filter 94 is tuned to pass a 3 Hz signal to the RMS voltage detector 95 connected thereto.

The different amplitude levels for the 1 Hz output of oscillator 94 are controlled by timer 96 in a manner similar to that discussed supra with regard to the manner in which timer 56 controls oscillator 52. For the voltages of oscillator 91 which cause only physisorption operation, i.e., voltages in the 1-100 mv range, the output signals of voltage detectors 58 and 59 are coupled by way of multiplexer 97 under the control timer 96. When timer 96 activates oscillator 91 so that the voltage applied by the oscillator across the electrodes of detector 91 reaches a sufficiently high level to also cause chemisorption operation, the voltages at the outputs of voltage detector 58, fundamental phase detector 59, and harmonic phase detectors 92, as well as harmonic amplitude detectors 93, are sequentially coupled through multiplexer 97 under the control of timer 96.

The DC signals at the output of multiplexer 97 are coupled in sequence to analog-to-digital converter 98 which supplies a multi-bit signal indicative of the amplitude of the input to the converter to bus 99. The output signal of converter 98 on bus 99 is supplied to computer-type network 101 which is similar to computer-type network 57.

The memory requirements of network 101 are considerably less than those of network 57. The signals on bus 99 indicative of the responses from detectors 58 and 59 while capacitor 51 is operated in only the physisorption mode are processed in virtually the same manner as the signals from converter 61 are processed by computer-type network 57. The signals on bus 99 for the physisorption only operating mode run through a gamut of amplitudes of the physisorption only mode, i.e., the signals on bus 99 represent the AC RMS voltage and the phase angle across resistor 54 for stepped amplitudes between 1 and 100 mv, at a 1 Hz excitation of capacitor 51. In the physisorption only mode, the output of RAM 66 is coupled directly to ROM 81 in response to switch 102 being controlled by timer 96 so that bus 82 is connected directly to the input of ROM 81.

When the chemisorption mode is added, the output signals of harmonic phase detectors 92 provide specie identification. The sequentially derived signals on lead 99 indicative of the harmonic phase shifts are stored in RAM 66 in the same manner as the responses from detectors 58 and 59. ROM 67 stores predetermined values for the harmonic phase detectors for the different species as a function of the amplitude of oscillator 91. These predetermined values for the harmonic phase detector outputs are compared with the output of RAM 66 by appropriate Tchebycheff distance calculators to enable the species incident on the detector 51 of FIG. 7 to be determined. Alternatively, step changes in the outputs of the harmonic phase detectors, i.e., changes greater than a predetermined amount, in response to step changes in the amplitude of the output of oscillator 91 are used when chemisorption specie identification is added. The step changes are detected by comparing the difference of the phase angle signals stored in a RAM for adjacent amplitude values of oscillator 91 with a reference that is a function of the adjacent amplitude values. In response to the difference exceeding the reference an indication is provided of the presence of a particular species that caused diode action of detector 51.

To determine concentration in the embodiment of FIG. 7, the amplitudes of the detected odd harmonics, as derived from voltage detectors 95 and converted into digital signals by converter 98, are accumulated. To this end, during processing of the data stored in RAM 66, timer 96 activates switch 102 so that the output bus of RAM 66 is coupled to accumulator 103. Accumulator 103 is coupled to the output bus 82 of RAM 66 by timer 96 only during the interval while the timer addresses the RAM to read out the values associated with the outputs of voltage detectors 95. The accumulated value for each amplitude applied to detector 51 when the chemisorption mode is added is stored at a separate address in RAM 104, which is addressed under the control of timer 96.

If several species to be detected are incident on detector 51, the responses in RAM 104 at each addressed value for the different amplitudes that cause detector diode like action represent accumulated effects of the several different species. Because the voltage across resistor 54 increases as the amplitude of the voltage of oscillator 91 increases as the oscillator voltages change from 0.1 to 3 volts, the different values stored in the different addresses of RAM 104 may be indicative of the effects of a single specie or plural species incident on capacitor 51. To determine concentration, the contents of RAM 104 are sequentially read out from the different RAM addresses and added together. The read out sequence progresses for increasing values of excitation voltages. The values from the different addresses of RAM 104 are added together until an identified specie is detected. The accumulated value for the identified specie is correlated with a concentration value associated with the accumulated value. The value associated with a particular specie is subtracted from the accumulated value as the read out process of RAM 104 continues to provide an amplitude value for the next detected specie.

The apparatus for providing this result includes accumulator 105, responsive to the output of RAM 104. Accumulator 105 has a multi-bit output that is supplied to buffer memory 106 which is provided for the gas specie having the lowest voltage causing diode action of detector 51. Buffer 106 is selectively enabled by the output of comparator 72 when the Tchebycheff distance or step change calculation indicates that the specie associated with buffer 106 is present. Buffer 106 is enabled only while multiplexer 73 is responsive to the Tchebycheff distance or step change calculator associated with the specie associated with buffer 106. The output of buffer 106 is coupled to read-only memory 107 which is essentially a single dimension lookup table correlating the amplitude value stored in buffer 106 with a concentration value for the specie associated with buffer 106.

The outputs of accumulator 105 and buffer memory 106 are respectively applied to minuend and subtrahend inputs of multi-bit digital difference network 108. If the specie associated with buffer 106 is present, the output of subtracting network 108 provides an indication of the concentration of a second gas specie incident on detector 51. If the specie associated with buffer 106 is indicated as not being present by the Tchebycheff distance or step change calculation process, the output of subtracting network 108 is equal to the contents of accumulator 105.

Difference network 108 derives a multi-bit output that is applied to buffer 109, associated with the gas specie causing diode action of detector 51 for the next highest output voltage of oscillator 52. Buffer 109 includes an enable input responsive to the Tchebycheff distance or step change calculation process associated with the gas causing the next highest voltage diode action of detector 51. Buffer 109 derives a multi-bit output that is supplied in parallel to ROM 111 and to an addend input of digital adder 112, having an augend input responsive to the output of buffer 106. Adder network 112 derives a multi-bit sum output that is applied to a subtrahend input of digital subtracting network 113, having a minuend input responsive to the output of accumulator 105. If the species associated with buffer 106 and 109 are both present, the output of adder 112 indicates the sum of the harmonic voltages associated with the voltage across resistor 54. The output of subtractor 113 is a signal having a value representing the contribution of the remaining gases on the harmonic voltages which have been read from RAM 104 to accumulator 105.

A network similar to that illustrated for the specie associated with buffer memory 109 is provided for each of the remaining species to be detected by detector 51, except that the network for the specie having the highest voltage for which diode action is initiated differs slightly from the other networks. In particular, the network for the specie having the highest voltage initiating diode action in detector 51 includes subtractor 115, having a minuend input responsive to the output of accumulator 105 and a subtrahend input responsive to the output of adder 116 of the network associated with the specie having the penultimate voltage causing diode action of detector 51. The multi-bit difference representing signal derived by subtraction network 115 is applied to buffer 117 which only drives read-only memory 118. ROM 118 is pre-programmed to correlate the binary signal coupled thereto to the concentration of the gas specie having the highest voltage inducing diode action in detector 51.

The specie quantitative measuring signals stored in ROMs 81, 107, 111 and 118 are supplied to quantitative numerical display 83 by way of multiplexing network 119 under the control of timer 96. Multiplexer 119 is energized in synchronism with display 79, so that when a particular gas specie is indicated on display 79 a corresponding numerical value representing concentration appears on display 83.

Reference is now made to FIG. 8 of the drawing wherein there is illustrated a further embodiment of a multigas gas analyzer in accordance with the present invention. The multigas gas analyzer of FIG. 8 includes an array of plural different capacitive gas detectors having ionic dielectrics. All of the detectors in the array are simultaneously responsive to all of the gases to be detected. The capacitors have different gas adsorbtion properties, preferably such that each detector is particularly adapted to detect a certain gas species or a small number of species. The different detectors thereby derive different output signals as a function of the gases incident thereon when activated to have diode like action and into the physisorption only mode by stepped variable amplitude and/or stepped variable frequency oscillator 52.

In particular, the gas detector of FIG. 8 includes detecting capacitors 121–125, all having lanthanum fluoride dielectrics and an electrode of differing materials covering the upper, exposed surface of the dielectric. The upper surface electrode of capacitor 121 is fabricated of an inert metal, e.g. gold. The upper surface electrode of capacitor 122 is covered with a porous zinc oxide catalytic layer, whereby capcitor 122 is particularly suited for methane detection. The upper surface electrode of capacitor 123 is covered with a palladium catalytic grid, whereby capacitor 123 is particularly suited for methane and hydrogen detection. The upper, exposed surface of capacitor 124 is covered with an electrode consisting of a catalytic iridium oxide layer, making capacitor 124 particularly suited for oxygen detection. Capacitor 125 is also particularly suited for oxygen detection, as the upper electrode thereof is formed of a Fe-phthalocyanine layer.

Capacitors 121–125 are selectively activated to have diode like action and into the physisorption only mode by the variable amplitude and/or variable frequency output of oscillator 52, connected to the capacitors by sampling resistor 54 and multiplexer 126. Multiplexer 126 selectively connects one of capacitors 121-125 to the output of oscillator 52 in response to a control signal supplied to the multiplexer by a timer in computer-type network 157. Computer-type network 157 responds to and processes output signal of voltage and phase detectors 58 and 59, via switch 62 in manners similar to those described supra for the computer-type networks of FIGS. 6 and 7. However, species are identified more accurately because capacitive detectors 122-125 are tailored for particular gases. Network 157 processes considerably more data than the networks of FIGS. 6 and 7 because network 157 is sequentially responsive to signals derived by detectors 58 and 59 for each of capacitors 121-125.

Network 157 controls oscillator 52 and multiplexer 126 so that a full range of amplitudes and/or frequencies of oscillator 52 is applied initially to capacitor 121. Network 157 initially collects data from detectors 58 and 59 while capacitor 121 is energized and the signal from detector 121 is coupled through multiplexer 126 to the network under the control of the timer in network 157. Then, network 157 energizes multiplexer 126 to connect detecting capacitor 122 to oscillator 52; the timer in network 157 then steps oscillator 52 through a full gamut of voltages and amplitudes. If methane is present, the response supplied to network 157 by detector 122 is appreciably different from the response with no methane. Network 157 may be programmed to supply the methane Tchebycheff distance calculator therein only with data collected from detector 122, rather than with data from all of the detectors, to simplify and shorten the processing operations. Signals from voltage and phase detectors 58 and 59 are collected by network 157 while capacitor 122 is energized. The stated sequence is repeated for each of capacitors 123-125.

After data have been collected by computer-type network 157 from capacitors 121-125, the computer is activated to read out data from the random access memory of the network. Network 157 compares the RAM output signals with predetermined values associated with the various species to be detected by capacitors 121-125 and derives a quantitative indication for each specie, as described supra in connection with FIGS. 6 and/or 7.

Figure 9:
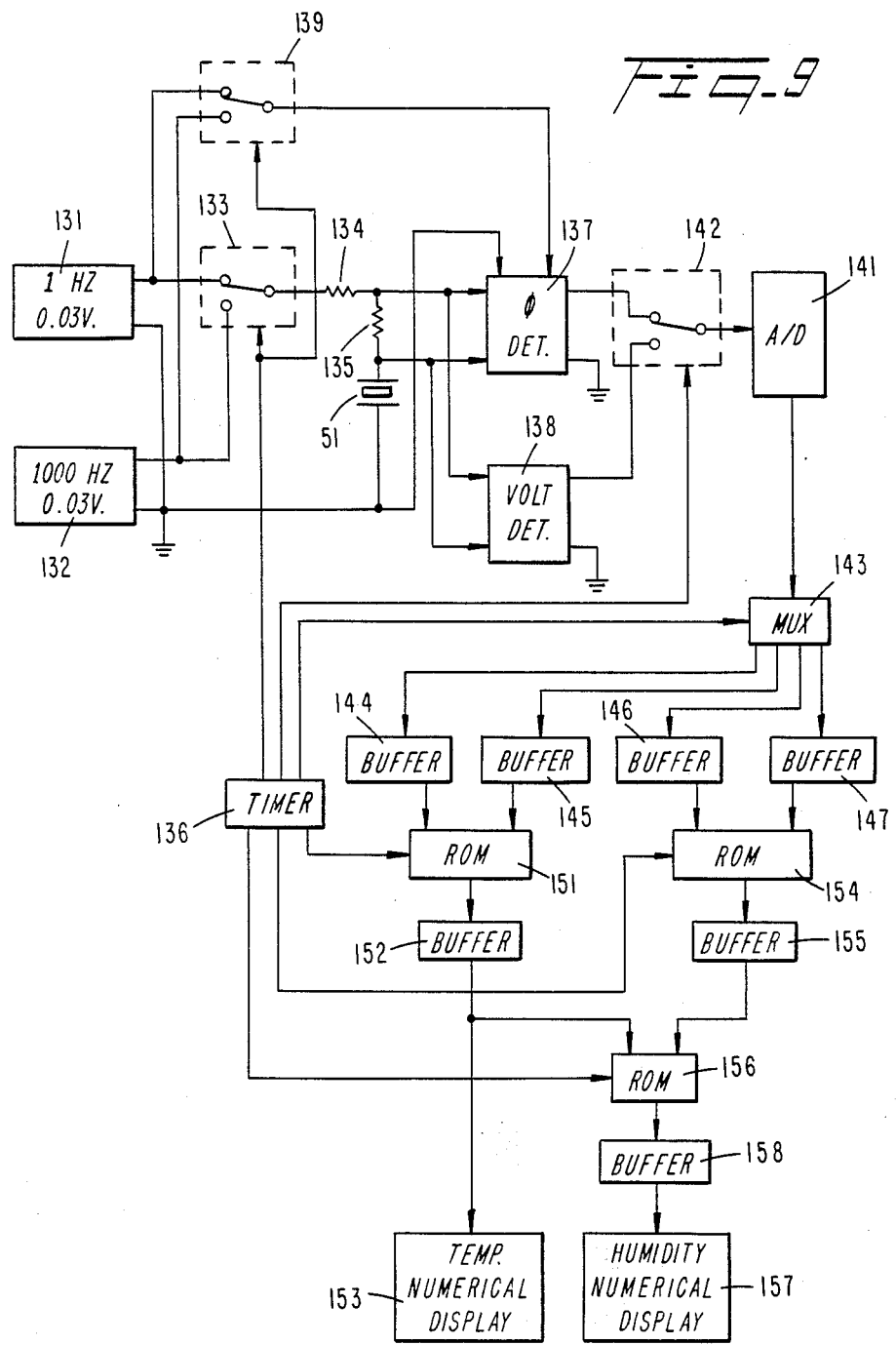
FIG. 9 is a partial circuit and partial block diagram of an embodiment of the invention for detecting both humidity and temperature, wherein a humidity sensing capacitor is operated in the physisorption mode such that at low frequencies both humidity and temperature are measured and at high frequencies only temperature is measured.

Reference is now made to FIG. 9 of the drawing wherein there is illustrated a circuit diagram for measuring the relative humidity and temperature of gases incident on capacitor 51 having a lanthanum fluoride dielectric and an inert metal, preferably gold top electrode. Capacitor 51 is activated into the physisorption only mode at frequencies of 1 Hz and 1000 Hz by oscillators 131 and 132, each of which impresses approximately a 3.0 millivolt AC RMS voltage across the electrodes of capacitor 51. The 1 Hz and 1000 Hz frequencies of oscillators 131 and 132 are selected because adsorbed water molecules are detected by the dielectric of capacitor 51 in response to the 1 Hz excitation, while the 1000 Hz response is insensitive to the presence of water. The 1000 Hz excitation causes capacitor 51 to have a response that is basically dependent upon an exponential function of temperature. In this regard, see the discussion supra with regard to FIG. 5.

Oscillators 131 and 132 are selectively coupled by switch 133 and sampling resistor 135 to capacitor 51 under the control of timer 136. The voltage across resistor 135 is applied in parallel to phase detector 137 and voltage detector 138. Phase detector 137 is also selectively and alternately responsive to the 1 Hz and 1000 Hz outputs of oscillators 131 and 132, by virtue of a connection to one input of the phase detector by way of switch 139. Switch 139 is controlled by timer 136 so that the output of oscillator 131 is simultaneously applied to capacitor 51 and phase detector 137 or the output of oscillator 132 is simultaneously supplied to the capacitor and phase detector. Phase detector 137 and voltage detector 138 derive DC output signals respectively indicative of the phase difference of the inputs thereof and the RMS AC input thereof. The output signals of detectors 137 and 138 are alternately applied to analog-to-digital converter 141 by way of switch 142 that is activated in synchronism with opening and closing of switches 133 and 139 by timer 136. Switch 142 couples the outputs of phase and voltage detectors 137 and 138 to converter 141 immediately prior to switches 133 and 139 changing state.

Converter 141 supplies a multi-bit signal representing the output voltages of detectors 137 and 138 to multiplexer 143 under the control of timer 136. Multiplexer 143 has four output buses, one of which is selectively connected by the multiplexer to the output bus of converter 141. The four output buses of multiplexer 143 are respectively applied to buffer memories 144-147, arranged to respond to the outputs of multiplexer 143 so that: (a) buffers 144 and 145 store phase and voltage signals representing the responses from phase detector 137 and voltage detector 138 while capacitor 51 is energized by 1000 Hz oscillator 132, and (b) buffers 146 and 147 store signals representing the output voltages of phase detector 137 and voltage detector 138 while capacitor 51 is energized by the 1 Hz output of oscillator 131.

The signals stored in buffers 144 and 145 are applied to read-only memory 151, which functions as a two-input table lookup having an enable input responsive to the output of timer 136. ROM 151 is enabled to respond to the signals stored in buffers 141 and 142 by timer 136 after the buffers have stored data representing the outputs of detectors 137 and 138 in response to the 1000 Hz excitation. ROM 151 is a lookup table relating the voltage and phase of the voltage across sampling resistor 135 in response to the 1000 Hz excitation to temperature. When enabled, ROM 151 derives a multi-bit output signal representing temperature; the multi-bit output signal of ROM 151 is supplied to buffer memory 152. Buffer memory 152 has a multi-bit output that is coupled to temperature numerical display 153.

Signals stored in buffers 146 and 147 indicative of the output voltages of detectors 137 and 138 in response to the 1 Hz excitation are supplied to ROM 154 when the ROM is enabled by an output of timer 136. ROM 154 is programmed to correlate water vapor on detector 151 with the outputs of detectors 137 and 138. The signals stored in ROM 154, however, do not represent relative humidity of the atmosphere to which detector 51 is exposed because the phase and voltage outputs of detectors 137 and 138 are a function of temperature.

To compensate for the temperature dependency of the water vapor indicating output of ROM 154, the output of the ROM is coupled to buffer memory 155 which supplies one input to ROM 156, having a second input responsive to the output of buffer 152. ROM 156 is programmed as a two-input lookup table relating the water vapor responses stored in ROM 154 to the temperature responses of ROM 151. ROM 156 is enabled by timer 136 after buffers 152 and 155 have been loaded by signals from ROMs 151 and 154. When enabled, ROM 156 derives an output signal representing relative humidity independently of temperature. The output of ROM 156 is supplied to humidity numerical display 157 by way of buffer memory 158.

While there have been described and illustrated several specific embodiments of the invention, it will be clear that variations in the details of the embodiments specifically illustrated and described may be made without departing from the true spirit and scope of the invention as defined in the appended claims.

We claim:

1. In a method of detecting the presence of a predetermined gas in an ambient gaseous environment with a capacitor having a solid gas adsorbing electrolyte dielectric, said predetermined gas and gases of the ambient environment interacting so there is a change in the adsorbtion of the ambient gases by the dielectric when the ambient gases and the predetermined gas are incident on the dielectric compared to the adsorbtion of the ambient gases when the predetermined gas is not incident on the dielectric and/or the predetermined gas is adsorbed by the dielectric when it is incident on the dielectric, the degree of adsorbtion being related to the amount of the predetermined gas incident on the dielectric, comprising the steps of: while said electrolyte dielectric is exposed to said predetermined gas to adsorb molecules of the gases of the ambient environment and/or the predetermined gas, energizing said capacitor to measure a physisorption process at said dielectric and molecules of the gases incident on and adsorbed by the dielectric, the capacitive impedance of said capacitor being affected by an interaction of the physisorption process and the gas molecules adsorbed by the dielectric; and deriving a response indicative of the value of the capacitive impedance of said capacitor as affected by the interaction of the physisorption process and the gas molecules adsorbed the dielectric, the derived response providing an indication of the presence of the predetermined gas.

2. The method of claim 1 wherein the capacitor is energized to measure the physisorption effect by supplying opposed electrodes of the capacitor with a voltage having a sufficiently low amplitude in a predetermined range so as not to drive gas molecules into the dielectric.

3. The method of claim 2 wherein the voltage is an AC voltage having a frequency sufficiently low to measure the effect of the physisorbed gas on space charge of the solid dielectric.

4. The method of claim 2 wherein the frequency is less than 30 Hz.

5. The method of claim 4 wherein the amplitude of the AC voltage is in the range of from 1 to 100 millivolts RMS.

6. The method of claim 2 wherein the amplitude of the voltage is in the range of from 1 to 100 millivolts.

7. The method of claim 1 wherein the dielectric is a rare earth fluoride.

8. Th method of claim 7 wherein there is a catalyst on the dielectric interacting with the gases to activate oxygen from the ambient environment incident on the dielectric.

9. The method of claim 8 wherein the catalyst is selected from the group consisting of ZnO, Pd, $IrO_2$, Fe-phthalocyanine, Co-phthalocyanine, $Fe_2O_3$, $SnO_2$, and CdS.

10. The method of claim 1 wherein the dielectric is lanthanum fluoride.

11. The method of claim 10 wherein there is a catalyst on the dielectric interacting with the gases to activate oxygen incident on the dielectric.

12. The method of claim 11 wherein the catalyst is selected from the group consisting of ZnO, Pd, $IrO_2$, Fe-phthalocyanine, Co-phthalocyanine, $Fe_2O_3$, $SnO_2$, and a metal sulfide.

13. The method of claim 11 wherein the predetermined gas is an oxygen atom containing gas specie and the catalyst is selected from the group consisting of $IrO_2$, Fe-phthalocyanine and Co-phthalocyanine.

14. The method of claim 13 wherein the dielectric and oxidizing gas are at room temperature.

15. The method of claim 11 wherein the predetermined gas is a reducing gas and the catalyst is selected from the group consisting of Pd, ZnO, $Fe_2O_3$ and $SnO_2$.

16. The method of claim 15 wherein the dielectric and reducing gas are at room temperature.

17. The method of claim 1 wherein the predetermined gas is oxygen and the catalyst is selected from the group consisting of $IrO_2$, Fe-phthalocyanine, and Co-phthalocyanine.

18. The method of claim 17 wherein the dielectric and oxygen are at room temperature.

19. The method of claim 1 wherein the predetermined gas is methane and the catalyst for promoting oxidation of the methane gas is selected from the group consisting of Pd, ZnO, $Fe_2O_3$ and $SnO_2$.

20. The method of claim 19 wherein the dielectric and methane are at room temperature.

21. The method of claim 1 further comprising the step of determining the concentration of the predetermined gas in the ambient gas by correlating the response indicative of the impedance of the capacitor with predetermined responses indicative of concentration for the predetermined gas.

22. The method of claim 1 wherein the resistive impedance of said capacitor is affected by an interaction of the physisorption process and the gas molecules adsorbed by the dielectric; the derived response being indicative of the value of the resistive impedance of said capacitor as affected by the interaction of the physisorption process and the gas molecules adsorbed the dielectric.

23. In a method of detecting the presence of a predetermined gas in an ambient gaseous environment with a capacitor having a solid gas adsorbing electrolyte dielectric, said predetermined gas and gases of the ambient environment interacting so there is a change in adsorption of the ambient gases by the dielectric when the ambient gases and the predetermined gas are incident on the dielectric compared to the adsorbtion of the ambient gases when the predetermined gas is not incident on the dielectric and/or the predetermined gas is adsorbed by the dielectric when it is incident on the dielectric, the degree of adsorbtion being related to the amount of the predetermined gas incident on the dielectric, comprising the steps of: while said dielectric is exposed to said predetermined gas to adsorb molecules of the gases of the ambient environment and/or the predetermined gas, applying AC excitation to said capacitor to cause an adsorption process to occur between said dielectric and molecules of the gases incident on and adsorbed by the dielectric, the AC impedance of said capacitor being affected by an interaction of the adsorption process and the gas molecules adsorbed by the dielectric; and deriving a response indicative of the value of the AC impedance of said capacitor as affected by the interaction of the adsorption process and the gas molecules adsorbed by the dielectric, the derived response providing an indication of the presence of the predetermined gas.

24. The method of claim 23 wherein the AC voltage has an amplitude which enables a physisorption process occurring on the dielectric to be measured.

25. The method of claim 24 wherein the capacitor is energized to measure the physisorption effect by supplying opposed electrodes of the capacitor with an AC voltage having a sufficiently low amplitude in a predetermined range so that chemisorption does not occur and gases are adsorbed by the dielectric only in response to van der Waals forces of attraction between the gases incident on the dielectric and the dielectric.

26. The method of claim 5 wherein the amplitude of the AC voltage is in the range of from 1 to 100 millivolts.

27. The method of claim 24 wherein the AC excitation is an AC voltage having a frequency sufficiently low to measure the effect thereof on space charge of the dielectric.

28. The method of claim 27 wherein the frequency is less than 30 Hz.

29. The method of claim 23 wherein the dielectric is a rare earth fluoride.

30. The method of claim 29 wherein there is a catalyst on the dielectric interacting with the gases to activate oxygen incident on the dielectric.

31. The method of claim 30 wherein the catalyst is selected from the group consisting of ZnO, Pd, IrO, Fe-phthalocyanine, and Co-phthalocyanine.

32. The method of claim 23 wherein the dielectric is lanthanum fluoride.

33. The method of claim 32 wherein there is a catalyst on the dielectric interacting with the gases to modify oxygen in the ambient environment incident on the dielectric.

34. The method of claim 33 wherein the catalyst is selected from the group consisting of ZnO, Pd, IrO, Fe-phthalocyanine, and Co-phthalocyanine.

35. The method of claim 33 wherein the predetermined gas is oxygen and the catalyst is selected from the group consisting of $IrO_2$, Fe-phthalocyanine, and Co-phthalocyanine.

36. The method of claim 35 wherein the dielectric and oxygen are at room temperature.

37. The method of claim 33 wherein the predetermined gas is methane and the catalyst is selected from the group consisting of Pd, ZnO, $Fe_2O_3$ and $SnO_2$.

38. The method of claim 37 wherein the dielectric and methane are at room temperature.

39. The method of claim 33 wherein the predetermined gas is an oxidizing gas and the catalyst is selected from the group consisting of $IrO_2$, Fe-phthalocyanine and Co-phthalocyanine.

40. The method of claim 39 wherein the dielectric and oxidizing gas are at room temperature.

41. The method of claim 33 wherein the predetermined gas is a reducing gas and the catalyst is selected from the group consisting of Pd, ZnO, $Fe_2O_3$ and $SnO_2$.

42. The method of claim 41 wherein the dielectric and reducing gas are at room temperature.

43. The method of claim 23 further comprising the step of determining the concentration of the predetermined gas in the ambient gas by correlating the response indicative of the impedance of the capacitor with predetermined responses indicative of concentration for the predetermined gas.

44. The method of claim 23 wherein the AC voltage causes the adsorption process to be a chemisorption process.

45. The method of claim 44 wherein the AC voltage has an amplitude sufficient to cause the capacitor to exhibit diode action without causing breakdown of the dielectric.

46. The method of claim 45 wherein the diode action causes harmonics of the AC to be derived by the capacitor, said response being derived in response to the harmonics caused by the diode action.

47. The method of claim 45 wherein the amplitude of the AC voltage is in the range of 0.1 to 3 volts RMS.

48. The method of claim 45 wherein the voltage is an AC voltage having a frequency sufficiently low to enable measurement of the chemisorption process on space charge of the dielectric.

49. The method of claim 45 wherein the dielectric is intrinsically doped.

50. The method of claim 45 wherein the dielectric is extrinsically doped.

51. A method of determining relative humidity of air with a capacitor sensor having a solid ionic dielectric exposed to the air comprising the steps of applying voltages having first and second predetermined frequency ranges to the capacitor sensor, the first frequency range and the amplitude thereof causing an impedance component of the capacitor sensor to vary as a function of air temperature and humidity, the second frequency range and the amplitude thereof causing an AC impedance component of the capacitor sensor to vary as a function of air temperature independently of humidity, deriving first and second responses respectively responsive to the magnitudes of said impedance components to the voltages in the first and second frequency ranges, and responding to indications of the magnitudes of the first and second responses to derive a quantitative measure of the relative humidity.

52. The method of claim 51 wherein the voltage amplitudes in the first and second frequency ranges are such that there is only physisorption of molecules in the air by the dielectric without causing electric field driven chemisorption by the dielectric of molecules on the dielectric.

53. The method of claim 51 wherein the voltage amplitudes in the first and second frequency ranges are sufficiently low to allow only water vapor in the air and molecules of the air to be adsorbed by the dielectric only in response to van der Waals forces of attracting between the gases incident on the dielectric and the dielectric.

54. The method of claim 43 wherein the amplitudes of the voltages in the first and second frequency ranges are between 1 and 100 millivolts.

55. The method of claim 53 wherein the first frequency range is sufficiently low as to allow water vapor molecules that are adsorbed to be detected by monitoring impedance component modifications at the first frequency range.

56. The method of claim 55 wherein the second frequency range is sufficiently high that physisorption induced impedance changes in the first frequency can not be monitored.

57. The method of claim 56 wherein the first frequency range is less than 30 Hz and the second frequency range is between 30 Hz and 6 kHz.

58. A method of determining the amount of a vapor having polar molecules in an ambient gaseous environment with a capacitor having a solid electrolyte dielectric for adsorbing molecules of said one vapor, comprising the steps of: while said dielectric is exposed to said vapor to adsorb molecules of said vapor energizing said capacitor to allow measurement of the physisorption process, the capacitor impedance of said capacitor being affected by an interaction of the physisorption process and gas molecules of said environment, measuring the value of the impedance of said capacitor including the capacitive impedance thereof as affected by the interaction of the physisorption process and the gas molecules of the environment, and correlating the measured impedance value with the amount of the vapor.

59. The method of claim 58 wherein the capacitor is energized to measure the physisorption effect by supplying opposed electrodes of the capacitor with an AC voltage having a low frequency in a predetermined range when gas molecules of the environment are adsorbed in response to van der Waals forces.

60. The method of claim 59 wherein the frequency is on the order of 1 Hz and the amplitude is in the range of about 10–30 millivolts.

61. The method of claim 58 wherein the resistive impedance of said capacitor is affected by an interaction of the physisorption process and gas molecules of said environment, measuring the value of the impedance of said capacitor, including the resistive impedance thereof, as affected by the interaction of the physisorption process and the gas molecules of the environment.

62. In a method of detecting reducing gas molecules in an ambient gaseous environment with a capacitor having a solid electrolyte dielectric, the dielectric being overlaid by a metal structure that interacts with the gas molecules to produce ions of molecules that can be adsorbed by the dielectric, the structure being constructed so that the dielectric is exposed to the reducing gas and the ambient gaseous environment, comprising the steps of while the capacitor is exposed to said reducing gas molecules and the ambient gaseous environment energizing said capacitor to cause an adsorption process to occur between the dielectric and said ions, the capacitive impedance of said capacitor being affected by an interaction of the adsorption process and said ions, and deriving a response indicative of the value of the impedance of said capacitor as affected by the interaction of the adsorption process and said ions, the derived response providing an indication of the presence of the reducing gas molecules.

63. The method of claim 62 wherein the resistive impedance of said capacitor is affected by an interaction of the adsorption process and said ions, wherein the derived response is indicative of the value of the resistive impedance of said capacitor as affected by the interaction of the adsorption process and said ions.

64. A method of determining relative humidity and temperature of air with a capacitor sensor including a solid ionic dielectric exposed to the air comprising the steps of monitoring a first impedance component of the sensor in response to a first excitation of the sensor which causes the impedance component to be a function of the air temperature and relative humidity, monitoring an AC impedance component of the sensor in response to AC excitation of the sensor at a frequency in a predetermined range, the first excitation measuring the effect of physisorption of gaseous molecules by the dielectric without causing field-driven chemisorption of gaseous molecules by the dielectric, the monitored AC impedance component in response to the AC excitation providing a measure of the temperature independent of the relative humidity, and combining values indicative of the monitored impedance components in response to both of said excitations.

65. The method of claim 64 wherein the first excitation is AC at a frequency in another range that is sufficiently low to allow water vapor molecules in the air to be sensed, the frequency of the predetermined range being sufficiently high to prevent sensing of adsorbed molecules on the dielectric.

66. The method of claim 65 wherein the another frequency range is less than 30 Hz and the predetermined frequency range is between 30 Hz and 6 kHz.

67. The method of claim 65 wherein the voltage amplitudes in the another and predetermined frequency range are sufficiently low to measure adsorbtion of molecules in the air on the dielectric only by van der Waals surface forces.

68. A method of determining gas temperature with a capacitor sensor including a solid ionic dielectric exposed to the gas comprising the steps of monitoring an impedance component of the sensor in response to AC excitation of the sensor, the AC excitation having a predetermined frequency range and a predetermined amplitude range, the predetermined amplitude range allowing physisorption of gaseous molecules by the dielectric without causing field-driven chemisorption of gaseous molecules on the dielectric, the predetermined frequency range being sufficiently high to prevent space charge of the dielectric from following it, the monitored impedance component in response to the AC excitation in the predetermined range providing a measure of the temperature independent of the relative humidity.

69. A method of measuring the amount of gases having polar molecules in an ambient gaseous environment with a capacitor sensor including a solid ionic dielectric exposed to gases in the environment comprising the steps of monitoring an impedance component of the sensor in response to excitation of the sensor by a voltage in a predetermined amplitude range, the amplitude of the excitation allowing physisorption of gaseous molecules by the dielectric without causing field-driven chemisorption of gaseous molecules by the dielectric, the monitored impedance component in response to the excitation providing a measure of the amount of the gases having the polar molecules in the ambient gaseous environment.

70. Apparatus for detecting the presence of a predetermined gas in an ambient gaseous environment comprising a capacitor having a solid gas adsorbing electrolyte dielectric, said predetermined gas and gases of the ambient environment interacting so there is a change in adsorbtion of the ambient gases on the dielectric when the ambient gases and the predetermined gas are incident on the dielectric compared to the adsorbtion of the ambient gases when the predetermined gas is not incident on the dielectric and/or the predetermined gas is adsorbed by the dielectric when it is incident on the dielectric, the degree of adsorbtion being related to the amount of the predetermined gas incident on the dielectric, means for applying an AC voltage to said capacitor while said dielectric is exposed to said predetermined gas to adsorb molecules of the gases of the ambient environment and/or the predetermined gas, the AC voltage energizing said capacitor so an adsorption process occurs between said dielectric and molecules of the gases incident on and adsorbed by the dielectric, the impedance of said capacitor being affected by an interaction of the adsorption process and the gas molecules adsorbed by the dielectric, and means for deriving a response indicative of the value of the AC impedance of said capacitor as affected by the interaction of the adsorption process and the gas molecules adsorbed the dielectric, the derived response providing an indication of the presence of the predetermined gas.

71. The apparatus of claim 70 wherein the response deriving means includes means for detecting the phase difference between the current through and voltage across the capacitor and the amplitude of the current through the capacitor.

72. The apparatus of claim 70 wherein the AC applying means includes means for varying the AC amplitude applied to the capacitor, and further including data processing means responsive to the responses for comparing the AC responses for different ones of the AC amplitudes with stored values thereof for different species and concentrations of gases as a function of the variable AC amplitude applied to the capacitor.

73. The apparatus of claim 72 wherein the AC applying means includes means for varying the AC frequency applied to the capacitor, and further including data processing means responsive to the responses for comparing the AC responses for different ones of the AC frequencies with stored values thereof for different species and concentrations of gases as a function of the variable AC frequency applied to the capacitor.

74. The apparatus of claim 70 wherein the AC applying means includes means for varying the AC frequency applied to the capacitor, and further including data processing means responsive to the responses for comparing the AC responses for different ones of the AC frequencies with stored values thereof for different species and concentrations of gases as a function of the variable AC frequency applied to the capacitor.

75. The apparatus of claim 70 wherein the AC applying means includes means for varying the AC amplitude applied to the capacitor, certain of the AC amplitudes causing diode action of the capacitor, the diode action causing derivation of harmonics of the AC frequency applied to the capacitor, and means responsive to a derived harmonic for and the AC voltage causing derivation of the harmonics for identifying the predetermined gas.

76. The apparatus of claim 70 wherein the AC voltage allows a chemisorption process to occur.

77. The apparatus of claim 70 wherein the AC voltage allows a physisorption process to occur.

78. Apparatus for detecting the presence of plural predetermined gases in an ambient gaseous environment comprising a plurality of capacitors having a solid gas adsorbing electrolyte dielectric, different ones of said predetermined gas and gases of the ambient environment interacting in a different manner on different ones of the capacitors so each capacitor has a preferential response to different ones of the gases, the interaction of each capacitor being such that there is a change in adsorbtion of the ambient gases by each dielectric when the ambient gases and the predetermined gas are incident on the dielectric compared to the adsorbtion of the ambient gases when the predetermined gas is not incident on the dielectric and/or the predetermined gas is adsorbed by the dielectric when it is incident on the dielectric, the degree of adsorbtion being related to the amount of the predetermined gas incident on the dielectric, means for applying an AC voltage to said capacitors while said dielectrics are exposed to said predetermined gases to adsorb molecules of the gases of the ambient environment and/or the predetermined gases, the AC voltage energizing said capacitors so adsorption processes occur between said dielectrics and molecules of the gases incident on and adsorbed by the dielectrics, the AC impedances of said capacitors being affected by an interaction of the adsorption process and the gas molecules adsorbed by the dielectrics, and means for deriving responses indicative of the values of the AC impedances of said capacitors as affected by the interactions of the adsorption processes and the gas molecules adsorbed by dielectrics, the derived responses providing an indication of the presence of the predetermined gases.

79. The apparatus of claim 78 wherein the AC voltage allows the adsorption processes to be a physisorption processes.

80. The apparatus of claim 79 wherein the capacitors are energized to allow the physisorption effect to occur by supplying opposed electrodes of the capacitors with an AC voltage having a sufficiently low amplitude in a predetermined range allowing the gases to be adsorbed by the dielectric only in response to van der Waals forces of attraction between the gases incident on the dielectric and the dielectric.

81. The apparatus of claim 78 wherein the AC voltage causes the adsorption processes to be a chemisorption processes.

82. The apparatus of claim 81 wherein the AC voltage has an amplitude sufficient to cause the capacitors to exhibit diode action without causing breakdown of the dielectric.

83. Apparatus for determining relative humidity of air comprising a capacitor sensor having a solid ionic dielectric exposed to the air, means for applying voltages having first and second predetermined frequency ranges to the capacitor sensor, the first frequency range and the amplitude thereof causing an impedance component of the capacitor sensor to vary as a function of air temperature and humidity, the second frequency range and the amplitude thereof causing an AC impedance component of the capacitor sensor to vary as a function of air temperature independently of humidity, means coupled to the capacitor sensor for deriving first and second responses respectively responsive to the magnitudes of said impedance components to the voltages in the first and second frequency ranges, and means responsive to indications of the magnitudes of the first and second responses for deriving a quantitative measure of the relative humidity.

84. The apparatus of claim 83 wherein the voltage amplitudes in the first and second frequency ranges are such that there is only physisorption of molecules in the air by the dielectric without causing electric field driven chemisorption by the dielectric of molecules on the dielectric.

85. The apparatus of claim 83 wherein the voltage amplitudes in the first and second frequency ranges are sufficiently low to allow only water vapor in the air and molecules of the air to be adsorbed by the dielectric only in response to van der Waals forces of attraction between the gases incident on the dielectric and the dielectric.

86. The apparatus of claim 85 wherein the amplitudes of the voltages in the first and second frequency ranges are between 1 and 100 millivolts.

87. The apparatus of claim 85 wherein the first frequency range is sufficiently low as to allow water vapor molecules that are adsorbed to be detected by monitoring impedance component modifications at the first frequency range.

88. The apparatus of claim 87 wherein the second frequency range is sufficiently high that physisorption induced impedance changes in the first frequency cannot be monitored.

89. The apparatus of claim 88 wherein the first frequency range is less than 30 Hz and the second frequency range is between 30 Hz and 6 kHz.

90. Apparatus for determining relative humidity and temperature of air comprising a capacitor sensor including a solid ionic dielectric exposed to the air, a source coupled to the sensor for providing predetermined first excitation of the sensor causing a first impedance component of the sensor to be a function of the air temperature and relative humidity and for AC exciting the sensor with a frequency in a predetermined range, the first impedance component being in response to a predetermined excitation exclusive of the AC exciting in said predetermined frequency range, the predetermined excitation enabling the effect of physisorption of gaseous molecules by the dielectric to be measured without causing field-driven chemisorption of gaseous molecules by the dielectric, the monitored AC impedance component in response to the AC excitation providing a measure of the temperature independent of the relative humidity, and means for combining values indicative of the monitored impedance components in response to both of said excitations.

91. The apparatus of claim 90 wherein the first excitation is AC at a frequency in another range that is sufficiently low to allow water vapor molecules in the air to be sensed, the frequency of the predetermined range being sufficiently high to prevent sensing of adsorbed molecules on the dielectric.

92. The apparatus of claim 91 wherein the another frequency range is less than 30 Hz and the predetermined frequency range is between 30 Hz and 6 kHz.

93. The apparatus of claim 92 wherein the voltage amplitudes in the another and predetermined frequency range are sufficiently low to measure adsorbtion of molecules in the air on the dielectric only by van der Waals surface forces.

94. Apparatus for determining gas temperature comprising a capacitor sensor including a solid ionic dielectric exposed to the gas, an AC excitation source coupled to the sensor, the AC excitation having a predetermined frequency range and a predetermined amplitude range, the predetermined amplitude range allowing physisorption of gaseous molecules by the dielectric without causing field-driven chemisorption of gaseous molecules on the dielectric, the predetermined frequency range being sufficiently high to prevent space charge of the dielectric from following it, means for monitoring an impedance component of the sensor in response to the AC excitation, the monitored impedance component in response to the AC excitation in the predetermined range providing a measure of the temperature independent of the relative humidity.

* * * * *